United States Patent
Zhang et al.

(10) Patent No.: US 7,452,914 B2
(45) Date of Patent: Nov. 18, 2008

(54) SPIRO-BENZO[C]CHROMENE DERIVATIVES USEFUL AS MODULATORS OF THE ESTROGEN RECEPTORS

(75) Inventors: Xuqing Zhang, Raritan, NJ (US); Zhihua Sui, Raritan, NJ (US)

(73) Assignee: Janssen Pharmaceutica N.V. (BE)

( * ) Notice: Subject to any disclaimer, the term of this patent is extended or adjusted under 35 U.S.C. 154(b) by 521 days.

(21) Appl. No.: 11/184,250

(22) Filed: Jul. 19, 2005

(65) Prior Publication Data

US 2006/0020018 A1    Jan. 26, 2006

Related U.S. Application Data

(60) Provisional application No. 60/560,753, filed on Jul. 19, 2004.

(51) Int. Cl.
*A61K 31/385* (2006.01)
*C07D 339/06* (2006.01)
*C07D 409/02* (2006.01)

(52) U.S. Cl. .................... 514/440; 549/29; 549/30; 549/35; 514/430; 514/438

(58) Field of Classification Search ............. 549/29, 549/30, 35; 514/430, 438, 440
See application file for complete search history.

(56) References Cited

FOREIGN PATENT DOCUMENTS

| WO | WO 02/053522 A2 | 7/2002 |
| WO | WO 02/053522 A3 | 7/2002 |
| WO | WO 02/066428 A2 | 8/2002 |
| WO | WO 02/066428 A3 | 8/2002 |
| WO | WO 2004/094400 A2 | 11/2004 |
| WO | WO 2004/094400 A3 | 11/2004 |

OTHER PUBLICATIONS

Albert, J.L. et al.: "Estrogen Regulation of Placental Alkaline Phosphatase Gene Expression in a Human Endometrial Adenocarcinoma Cell Line"; Cancer Research (Jun. 1, 1990) 50: 3306-3310.

Welshons, W.V. et al.: "Stimulation of breast cancer cells in vitro by the environmental estrogen entrolactone and the phytoestrogen equol"; Breast Cancer Research and Treatment (1987) 10: 169-175.

*Primary Examiner*—Golam M Shameem

(57) ABSTRACT

The present invention is directed to novel spiro-benzo[C] chromene derivatives, pharmaceutical compositions containing them and their use in the treatment of disorders mediated by one or more estrogen receptors. The compounds of the invention are useful in the treatment of disorders associated with the depletion of estrogen such as hot flashes, vaginal dryness, osteopenia and osteoporosis; hormone sensitive cancers and hyperplasia of the breast, endometrium, cervix and prostate; endometriosis, uterine fibroids, osteoarthritis and as contraceptive agents, alone or in combination with a progestogen or progestogen antagonist.

7 Claims, No Drawings

SPIRO-BENZO[C]CHROMENE DERIVATIVES USEFUL AS MODULATORS OF THE ESTROGEN RECEPTORS

CROSS REFERENCE TO RELATED APPLICATIONS

This application claims the benefit of U.S. Provisional Application 60/560,753, filed on Jul. 19, 2004, which is incorporated by reference herein in its entirety.

FIELD OF THE INVENTION

The present invention is directed to novel spiro-benzo[c]chromene derivatives, pharmaceutical compositions containing them and their use in the treatment or prevention of disorders and diseases mediated by an estrogen receptor such as hot flashes, vaginal dryness, osteopenia, osteoporosis, hyperlipidemia, loss of cognitive function, degenerative brain diseases, cardiovascular diseases, cerebrovascular diseases, hormone sensitive cancers and hyperplasia (in tissues including breast, endometrium, and cervix in women and prostate in men), endometriosis, uterine fibroids, osteoarthritis; and as contraceptive agents either alone or in combination with a progestogen or progestogen antagonist. The compounds of the invention are selective estrogen receptor modulators.

BACKGROUND OF THE INVENTION

Estrogens are a group of female hormones essential for the reproductive process and for the development of the uterus, breasts, and other physical changes associated with puberty. Estrogens have an effect on various tissues throughout a woman's body, not only those involved in the reproductive process, such as the uterus, breasts, and external genitalia, but also tissues in the central nervous system, bones, the liver, skin, and the urinary tract. The ovaries produce most of the estrogens in women's body.

Endogenous estrogens, such as 17β-estradiol and estrone, play a central role in the development of and maintenance of the female sex organs, mammary glands, and other sexual characteristics. In addition to their role as female sex hormone, estrogens are involved in the growth and function of a number of other tissues, such as the cardiovascular system, the central nervous system, and the skeleton, both in females and males. The significance of the estrogens in the development of the female reproductive system led to the development of a variety of compounds that interact with the estrogen receptors, such as contraceptives and agents for treatment of breast cancers. More recently, intensive efforts have focused on the selective estrogen receptor modulators for treatment and prevention of postmenopausal conditions, such as osteoporosis, coronary artery disease, depression and Alzheimer disease.

Menopause is defined as the permanent cessation of menses due to loss of ovarian follicular function and the almost termination of estrogen production. The midlife transition of menopause is characterized by a decrease in estrogen that provokes both short-term and long-term symptoms with the vasomotor, urogenital, cardiovascular, skeletal and central nervous systems, such as hot flushes, urogenital atrophy, increased risk of cardiovascular disease, osteoporosis, cognitive and psychological impairment, including an increased risk of cognitive disorders and Alzheimer's disease (AD).

Seventy-five percent of all women experience some occurrence of vasomotor symptoms associated with the onset of menopause such as body sweating and hot flushes. These complaints may begin several years before menopause and in some women may continue for more than 10 years either relatively constant, or as instant attacks without a definable, provoking cause.

Urogenital symptoms associated with the onset of menopause involving the vagina include a sensation of dryness, burning, itching, pain during intercourse, superficial bleeding and discharge, along with atrophy and stenosis. Symptoms involving the urinary tract include a burning sensation during urination, frequent urgency, recurrent urinary tract infections, and urinary incontinence. These symptoms have been reported to occur in up to 50% of all women near the time of menopause and are more frequent a few years after menopause. If left untreated, the problems can become permanent.

Heart attack and stroke are major causes of morbidity and mortality among senior women. Female morbidity from these diseases increases rapidly after menopause. Women who undergo premature menopause are at greater coronary risk than menstruating women of similar age. The presence of serum estrogen has a positive effect on serum lipids. The hormone promotes vasodilation of blood vessels, and enhances the formation of new blood vessels. Thus the decrease in serum estrogen levels in postmenopausal women results in adverse cardiovascular effect. Additionally, it is theorized that differences in the ability of blood to coagulate may account for the observed difference in the occurrence of heart disease before and after menopause.

The skeleton is under a continuous process of bone degeneration and regeneration in a carefully regulated interaction among the bone cells. These cells are directly affected by estrogen. Estrogen deficiency results in a loss of bone structure and a decrease of bone strength. Rapid loss of bone mass during the year immediately following menopause leads to postmenopausal osteoporosis and increased risk of fracture.

Estrogen deficiency is also one of the causes for the degenerative changes in the central nervous system and may lead to Alzheimer's disease and decline of cognition. Recent evidence suggests an association between estrogen, menopause and cognition. More particularly, it has been reported that estrogen replacement therapy and the use of estrogen in women may prevent the development of AD and improve cognitive function.

Hormone replacement therapy (HRT)—more specifically estrogen replacement therapy (ERT)—is commonly prescribed to address the medical problems associated with menopause, and also to help hinder osteoporosis and primary cardiovascular complications (such as coronary artery disease) in both a preventive and therapeutical manner. As such, HRT is considered a medical therapy for prolonging the average life span of postmenopausal women and providing a better quality of life.

ERT effectively relieves the climacteric symptoms and urogenital symptoms and has shown significant benefits in the prevention and treatment of heart disease in postmenopausal women. Clinical reports have shown that ERT lowered heart attack rates and mortality rates in populations that received ERT versus similar populations not on ERT. ERT initiated soon after menopause may also help maintain bone mass for several years. Controlled investigations have shown that treatment with ERT has a positive effect even in older women up to age of 75 years.

However, there are numerous undesirable effects associated with ERT that reduce patient compliance. Venous thromboembolism, gallbladder disease, resumption of menses, mastodynia and a possible increased risk of developing uterine and/or breast cancer are the risks associated with ERT. Up to 30% of women who were prescribed ERT did not fill the prescription, and the discontinuation rate is between 38% and 70%, with safety concerns and adverse effects (bloating and break-through bleeding) the most important reasons for discontinuation.

A new class of pharmacological agents known as Selective Estrogen Receptor Modulators or SERMs have been designed and developed as alternatives for HRT. Raloxifene, a nonsteroidal benzothiophere SERM is marketed in the US and Europe for the prevention and treatment of osteoporosis under the trademark of Evista®. Raloxifene has been shown to reduce bone loss and prevent fracture without adversely stimulating endometrial and mammary tissue, though raloxifene is somewhat less efficacious than ERT for protecting against bone loss. Raloxifene is unique and differs significantly from ERT in that it does not stimulate the endometrium and has the potential for preventing breast cancer. Raloxifene has also demonstrated beneficial estrogen agonist effects on cardiovascular risk factors, more specifically through a rapid and sustained decrease in total and low-density lipoprotein cholesterol levels in patients treated with raloxifene. In addition, raloxifene has been shown to reduce plasma concentration of homocysteine, an independent risk factor for arteriosclerosis and thromboembolic disease.

However, raloxifene has been reported to exacerbate symptoms associated with menopause such as hot flushes and vaginal dryness, and does not improve cognitive function in senior patients. Patients taking raloxifene have reported higher rates of hot flashes compared with either placebo or ERT users and more leg cramps than placebo users, although women who took ERT had a higher incidence of vaginal bleeding and breast discomfort than raloxifene or placebo users.

As yet, neither raloxifene nor any of the other currently available SERM compounds has been shown to have the ability to provide all the benefits of currently available ERT such as controlling postmenopausal syndrome and preventing AD, without causing adverse side effects such as increasing risk of endometrial and breast cancer and bleeding. Thus there exists a need for compounds which are selective estrogen receptor modulators and which provide all of the benefits of ERT while also addressing the vasomotor, urogenital and cognitive disorders or conditions associated with the decrease in systemic estrogen associated with menopause.

SUMMARY OF THE INVENTION

The present invention is directed to a compound of formula (I)

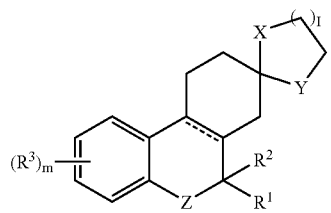

wherein

- - - - represents a single or double bond,

X, Y are selected from the group consisting of O, S, SO and $SO_2$;

Z is selected from the group consisting of O and S;

$R^1$ is selected from the group consisting of hydrogen, alkyl, cycloalkyl, aryl, aralkyl, heteroaryl and heteroaryl-alkyl; wherein the cycloalkyl, aryl, aralkyl, heteroaryl or heteroaryl-alkyl group is optionally substituted with one or more substituents independently selected from halogen, hydroxy, alkyl, alkoxy, —SH, —S(alkyl), $SO_2$, $NO_2$, CN, $CO_2H$, $R^C$, —$OR^C$, —$SO_2$—$NR^DR^E$, —$NR^DR^E$, $NR^D$—$SO_2$—$R^F$, $(alkyl)_{0-4}$-C(O)$NR^DR^E$, $(alkyl)_{0-4}$-$NR^D$—C(O)—$R^F$, -$(alkyl)_{0-4}$-$(Q)_{0-1}$-$(alkyl)_{0-4}$-$NR^DR^E$, -$(alkyl)_{0-4}$-$(Q)_{0-1}$-$(alkyl)_{0-4}$-C(O)—$OR^F$, -$(alkyl)^{0-4}$-$(Q)_{0-1}$-$(alkyl)_{0-4}$-C(O)-$NR^DR^E$ or -$(alkyl)_{0-4}$-C(O)-$(alkyl)_{0-4}$-C(O)—$OR^F$;

wherein $R^C$ is selected from the group consisting of alkyl, cycloalkyl, cycloalkyl-alkyl, aryl, aralkyl, heteroaryl, heteroaryl-alkyl, heterocycloalkyl and heterocycloalkyl-alkyl; wherein the cycloalkyl, cycloalkyl-alkyl, aryl, aralkyl, heteroaryl, heteroaryl-alkyl, heterocycloalkyl or heterocycloalkyl-alkyl group is optionally substituted with one or more substituents independently selected from halogen, hydroxy, alkyl, alkoxy, —SH, —S(alkyl), $SO_2$, $NO_2$, CN, $CO_2H$, $R^C$, —$SO_2$—$NR^DR^E$, $NR^DR^E$, $NR^DSO_2$—$R^F$, -$(alkyl)_{0-4}$-C(O)—$NR^DR^E$, -$(alkyl)_{0-4}$-$NR^D$—C(O)—$R^F$, -$(alkyl)_{0-4}$-$(Q)_{0-1}$-$(alkyl)_{0-4}$-$NR^DR^E$, -$(alkyl)_{0-4}$-$(Q)_{0-1}$-$(alkyl)_{0-4}$-C(O)—$OR^F$, -$(alkyl)^{0-4}$-$(Q)_{0-1}$-$(alkyl)_{0-4}$-C(O)—$NR^DR^E$ or -$(alkyl)_{0-4}$-C(O)-$(alkyl)_{0-4}$-C(O)—$OR^F$;

wherein Q is selected from the group consisting of O, S, NH, N(alkyl) and —CH=CH—;

wherein $R^D$ and $R^E$ are each independently selected from the group consisting of hydrogen and alkyl; alternatively $R^D$ and $R^E$ are taken together with the nitrogen atom to which they are bound to form a 4 to 8 membered ring selected from the group consisting of heteroaryl or heterocycloalkyl; wherein the heteroaryl or heterocycloalkyl group is optionally substituted with one or more substituents independently selected from halogen, hydroxy, alkyl, alkoxy, carboxy, amino, alkylamino, dialkylamino, nitro or cyano;

wherein $R^F$ is selected from the group consisting of hydrogen, alkyl, cycloalkyl, cycloalkyl-alkyl, aryl, aralkyl, heteroaryl, heteroaryl-alkyl, heterocycloalkyl and heterocycloalkyl-alkyl; wherein the cycloalkyl, aryl, heteroaryl, heteroaryl-alkyl, heterocycloalkyl or heterocycloalkyl-alkyl group is optionally substituted with one or more substituents independently selected from halogen, hydroxy, alkyl, alkoxy, carboxy, amino, alkylamino, dialkylamino, nitro or cyano;

$R^2$ is selected from the group consisting of hydroxy, alkyl, cycloalkyl, aryl, aralkyl, heteroaryl and heteroaryl-alkyl; wherein the cycloalkyl, aryl, aralkyl, heteroaryl or heteroaryl-alkyl group is optionally substituted with one or more substituents independently selected from halogen, hydroxy, alkyl, alkoxy, —SH, —S(alkyl), $SO_2$, $NO_2$, CN, $CO_2H$, $R^C$, —$OR^C$, —$SO_2$—$NR^DR^E$, —$NR^DR^E$, $NR^D$—$SO_2$—$R^F$, -$(alkyl)_{0-4}$-C(O)$NR^DR^E$, $(alkyl)_{0-4}$-$NR^D$—C(O)—$R^F$, -$(alkyl)_{0-4}$-$(Q)_{0-1}$-$(alkyl)_{0-4}$-$NR^DR^E$, -$(alkyl)_{0-4}$-$(Q)_{0-1}$-$(alkyl)_{0-4}$-C(O)—$OR^F$, -$(alkyl)_{0-4}$-$(Q)_{0-1}$-$(alkyl)_{0-4}$-C(O)—$NR^DR^E$ or -$(alkyl)_{0-4}$-C(O)-$(alkyl)_{0-4}$-C(O)—$OR^F$;

alternatively, $R^1$ and $R^2$ are taken together with the carbon atom to which they are bound to form C(O);

m is an integer selected from 0 to 4;

$R^3$ is independently selected from the group consisting of halogen, hydroxy, $R^C$, amino, alkylamino, dialkylamino, nitro, cyano, $SO_2$, —C(O)$R^G$, —C(O)$OR^G$, —OC(O)$R^G$, —OC(O)$OR^G$, —OC(O)N($R^G$)$_2$, —N($R^G$)C(O)$R^G$, —OSi($R^G$)$_3$—$OR^G$, —$SO_2N(R^G)_2$, —O-$(alkyl)_{1-4}$-C(O)$R^G$ and —O-$(alkyl)_{1-4}$C(O)$OR^G$;

wherein each $R^G$ is independently selected from hydrogen, alkyl, aryl, aralkyl and 1,7,7-trimethyl-2-oxabicyclo[2.2.1]heptan-3-one; wherein the alkyl, aryl or aralkyl group is optionally substituted with one or more substituents independently selected from alkyl, halogenated alkyl, alkoxy, halogen, hydroxy, nitro, cyano, —OC(O)-alkyl or —C(O)O-alkyl;

alternatively two $R^G$ groups are taken together with the nitrogen atom to which they are bound to form a heterocycloalkyl group; wherein the heterocycloalkyl group is optionally substituted with one or more substituents independently selected from halogen, hydroxy, alkyl, alkoxy, carboxy, amino, alkylamino, dialkylamino, nitro or cyano;

I is an integer selected from 0, 1;

In one aspect, the invention is a pharmaceutical composition comprising a pharmaceutically acceptable carrier and any of the compounds described above. In a second aspect, the invention is a pharmaceutical composition made by mixing any of the compounds described above and a pharmaceutically acceptable carrier. In another aspect, the invention is a process for making a pharmaceutical composition comprising mixing any of the compounds described above and a pharmaceutically acceptable carrier.

The invention also provides methods of treating a disorder mediated by one or more estrogen receptors in a subject in need thereof comprising administering to the subject a therapeutically effective amount of any of the compounds or pharmaceutical compositions described above.

One embodiment of this aspect of the invention is a method of contraception comprising administering to a subject in need thereof co-therapy with a therapeutically effective amount of a compound of formula (I) with a progestogen or progestogen antagonist.

The invention also relates to the use of any of the compounds described herein in the preparation of a medicament for treating: (a) hot flashes, (b) vaginal dryness, (c) osteopenia, (d) osteoporosis, (e) hyperlipidemia, (f) loss of cognitive function, (g) a degenerative brain disorder, (h) cardiovascular disease, (i) cerebrovascular disease (j) breast cancer, (k) endometrial cancer, (l) cervical cancer, (m) prostate cancer, (n) benign prostatic hyperplasia, (o) endometriosis, (p) uterine fibroids, (q) osteoarthritis and for (r) contraception in a subject in need thereof.

DETAILED DESCRIPTION OF THE INVENTION

The present invention is directed to a compound of formula (I)

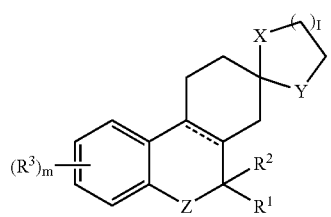

wherein X, Y, Z, $R^1$, $R^2$, $R^3$, m, and I are as herein defined, useful for the treatment of disorders mediated by an estrogen receptor. More particularly, the compounds of the present invention are useful for the treatment and prevention of disorders mediated by the estrogen-α and estrogen-β receptors. More preferably, the compounds of the present invention are tissue selective estrogen receptor modulators.

The compounds of the present invention are useful in the treatment of disorders associated with the depletion of estrogen, hormone sensitive cancers and hyperplasia, endometriosis, uterine fibroids, osteoarthritis and as contraceptive agents, alone or in combination with a progestogen or progestogen antagonist.

More particularly, the compounds of the present invention are useful in the treatment of a condition or disorder selected from the group consisting of hot flashes, vaginal dryness, osteopenia, osteoporosis, hyperlipidemia, loss of cognitive function, degenerative brain diseases, cardiovascular diseases, cerebrovascular diseases, cancer or hyperplasia of the breast tissue, cancer or hyperplasia of the endometrium, cancer or hyperplasia of the cervix, cancer or hyperplasia of the prostate, endometriosis, uterine fibroids and osteoarthritis; and as a contraceptive agent. Preferably, the disorder is selected from the group consisting of osteoporosis, hot flashes, vaginal dryness, breast cancer, and endometriosis.

In the compound of formula (I), the relative orientation of the groups $R^1$ and $R^2$ is not intended to be fixed, rather both possible orientations of the groups are intended to be included within the definition of the compound of formula (I).

In an embodiment of the present invention are compounds of formula (I) wherein X is S, Y is S and Z is O. In another embodiment of the present invention are compounds of formula (I) wherein X is O, Y is O and Z is O.

In an embodiment of the present invention $R^1$ is selected from the group consisting of hydrogen and lower alkyl. Preferably, $R^1$ is hydrogen.

In an embodiment of the present invention $R^1$ is hydrogen and $R^2$ is in the R stereo-configuration. In another embodiment of the present invention $R^1$ is hydrogen and $R^2$ is in the S stereo-configuration.

In an embodiment of the present invention $R^1$ is selected from the group consisting of hydrogen, lower alkyl, aryl, aralkyl, heteroaryl and heteroaryl-(lower alkyl); wherein the aryl, aralkyl, heteroaryl or heteroaryl-(lower alkyl) group is optionally substituted with one to two substituents independently selected from halogen, hydroxy, lower alkyl, lower alkoxy, —SH, —S(lower alkyl), $SO_2$, $NO_2$, CN, $CO_2H$, $R^C$, —$SO^2$—$NR^DR^E$, —$NR^DR^E$, $NR^D$—$SO_2$—$R^F$, -(alkyl)$_{0-4}$-C(O)$NR^DR^E$, (alkyl)$_{0-4}$-$NR^D$—C(O)—$R^F$, -(alkyl)$_{0-4}$-(Q)$_{0-1}$-(alkyl)$_{0-4}$-$NR^DR^E$, -(alkyl)$_{0-4}$-(Q)$_{0-1}$-(alkyl)$_{0-4}$-C(O)—$OR^F$, -(alkyl)$_{0-4}$-(Q)$_{0-1}$-(alkyl)$_{0-4}$-C(O)—$NR^DR^E$ or -(alkyl)$_{0-4}$-C(O)-(alkyl)$_{0-4}$-C(O)—$OR^F$.

Preferably $R^1$ is selected from the group consisting of hydrogen, lower alkyl, aryl, aralkyl, heteroaryl and heteroaryl-(lower alkyl); wherein the aryl, aralkyl, heteroaryl or heteroaryl-(lower alkyl) group is optionally substituted with one to two substituents independently selected from halogen, hydroxy, lower alkyl, lower alkoxy, —SH, —S(lower alkyl), $SO_2$, $NO_2$, CN, $CO_2H$, $R^C$ or $NR^DR^E$, More preferably $R^1$ is selected from the group consisting of hydrogen and lower alkyl. More preferably still $R^1$ is selected from the group consisting of hydrogen and methyl.

In an embodiment of the present invention $R^C$ is selected from the group consisting of lower alkyl, aryl, aralkyl, heteroaryl, heteroaryl-(lower alkyl), heterocycloalkyl and heterocycloalkyl-(lower alkyl); wherein the aryl, aralkyl, heteroaryl, heteroaryl-(lower alkyl), heterocycloalkyl or heterocycloalkyl-(lower alkyl) group is optionally substituted with one to two substituents independently selected from halogen, hydroxy, lower alkyl, lower alkoxy, —SH, —S(alkyl), $SO_2$, $NO_2$, CN, $CO_2H$, $R^C$, —$SO_2$—$NR^DR^E$, $NR^D$—$SO_2$—$R^F$, -(alkyl)$_{0-4}$-C(O)—$NR^DR^E$, -(alkyl)$_{0-4}$-$NR^D$—C(O)—$R^F$, -(alkyl)$_{0-4}$-(Q)$_{0-1}$-(alkyl)$_{0-4}$-$NR^DR^E$, -(alkyl)$_{0-4}$-(Q)$_{0-1}$-(alkyl)$_{0-4}$-C(O)—$OR^F$, -(alkyl)$_{0-4}$-(Q)$_{0-1}$-(alkyl)$_{0-4}$-C(O)—$NR^DR^E$ or -(alkyl)$_{0-4}$-C(O)-(alkyl)$_{0-4}$-C(O)—$OR^F$.

Preferably, $R^C$ is selected from the group consisting of lower alkyl, aryl, aralkyl, heteroaryl, heteroaryl-(lower alkyl), heterocycloalkyl and heterocycloalkyl-(lower alkyl); wherein the aryl, aralkyl, heteroaryl, heteroaryl-(lower alkyl), heterocycloalkyl or heterocycloalkyl-(lower alkyl) group is optionally substituted with one to two substituents independently selected from halogen, hydroxy, lower alkyl, lower alkoxy, —SH, —S(alkyl), $SO_2$, $NO_2$, CN, $CO_2H$, $R^C$ or $NR^D R^E$.

In an embodiment of the present invention, Q is selected from the group consisting of O, S and —CH═CH—. Preferably, Q is selected from the group consisting of O and —CH═CH—, more preferably Q is O.

In an embodiment of the present invention $R^D$ and $R^E$ are each independently selected from the group consisting of hydrogen and lower alkyl. In another embodiment of the present invention, $R^D$ and $R^E$ are taken together with the nitrogen atom to which they are bound to form a 5 to 6 membered ring selected from the group consisting of heteroaryl or heterocycloalkyl; wherein the heteroaryl or heterocycloalkyl group is optionally substituted with one to two substituents independently selected from halogen, hydroxy, lower alkyl, lower alkoxy, carboxy, amino, (lower alkyl)-amino, di(lower alkyl)amino, nitro or cyano.

In an embodiment of the present invention $R^F$ is selected from the group consisting of hydrogen, lower alkyl, aryl, aralkyl, heteroaryl, heteroaryl-(lower alkyl), heterocycloalkyl and heterocycloalkyl-(lower alkyl); wherein the aryl, heteroaryl, heteroaryl-(lower alkyl), heterocycloalkyl or heterocycloalkyl-(lower alkyl) group is optionally substituted with one to two substituents independently selected from halogen, hydroxy, lower alkyl, lower alkoxy, carboxy, amino, (lower alkyl)-amino, di(lower alkyl)amino, nitro or cyano.

In an embodiment of the present invention $R^2$ is selected from the group consisting of hydroxy, lower alkyl, aryl, aralkyl, heteroaryl and heteroaryl-(lower alkyl); wherein the aryl, aralkyl, heteroaryl or heteroaryl-(lower alkyl) group is optionally substituted with one to two substituents independently selected from halogen, hydroxy, lower alkyl, lower alkoxy, —SH, —S(lower alkyl), $SO_2$, $NO_2$, CN, $CO_2H$, $R^C$, —$OR^C$, —$SO_2$—$NR^D R^E$, —$NR^D R^E$, -(alkyl)$_{0-4}$-C(O)N$R^D R^E$, (alkyl)$_{0-4}$-$NR^D$—C(O)—$R^F$, -(alkyl)$_{0-4}$-(Q)$_{0-1}$-(alkyl)$_{0-4}$-$NR^D R^E$, -(alkyl)$_{0-4}$-(Q)$_{0-1}$-(alkyl)$_{0-4}$-C(O)—$OR^F$, -(alkyl)$_{0-4}$-(Q)$_{0-1}$-(alkyl)$_{0-4}$-C(O)—$NR^D R^E$ or -(alkyl)$_{0-4}$-C(O)-(alkyl)$_{0-4}$-C(O)—$OR^F$. Preferably, $R^2$ is selected from the group consisting of hydroxy, lower alkyl, aryl, aralkyl, heteroaryl and heteroaryl-(lower alkyl); wherein the aryl, aralkyl, heteroaryl or heteroaryl-(lower alkyl) group is optionally substituted with one to two substituents independently selected from halogen, hydroxy, lower alkyl, lower alkoxy, —SH, —S(lower alkyl), $SO_2$, $NO_2$, CN, $CO_2H$, $R^C$, —$OR^C$ or —$NR^D R^E$. More preferably, $R^2$ is selected from the group consisting of hydroxy, aryl, 4-(1-heterocycloalkyl-alkoxy)-phenyl, 4-(di(alkyl)amino-alkoxy)-phenyl, 4-(di(alkyl)amino)-phenyl and 4-aralkyloxy-phenyl. More preferably still, $R^2$ is selected from the group consisting of hydroxy, phenyl, 4-(1-piperidinyl-ethoxy)-phenyl, 4-(1-pyrrolidinyl-ethoxy)-phenyl, 4-(4-morpholinyl-ethoxy)-phenyl, 4-(1-azepinyl-ethoxy)-phenyl, 4-(diethylamino-ethoxy)-phenyl, 4-(dimethylamino-ethoxy)-phenyl, 4-(dimethylamino)-phenyl, 4-benzyloxy-phenyl and 4-(1-piperidinyl-n-propoxy)-phenyl. More preferably still, $R^2$ is selected from the group consisting of phenyl, 4-(1-piperidinyl-ethoxy)-phenyl, 4-(1-pyrrolidinyl-ethoxy)-phenyl, 4-(4-morpholinyl-ethoxy)-phenyl, 4-(1-azepinyl-ethoxy)-phenyl, 4-(diethylamino-ethoxy)-phenyl, 4-(dimethylamino-ethoxy)-phenyl, 4-(dimethylamino)-phenyl and 4-(1-piperidinyl-n-propoxy)-phenyl. More preferably still, $R^2$ is selected from the group consisting of phenyl, 4-(1-piperidinyl-ethoxy)-phenyl, 4-(1-pyrrolidinyl-ethoxy)-phenyl, 4-(4-morpholinyl-ethoxy)-phenyl, 4-(1-azepinyl-ethoxy)-phenyl, 4-(diethylamino-ethoxy)-phenyl, 4-(dimethylamino-ethoxy)-phenyl and 4-(dimethylamino)-phenyl. More preferably still, $R^2$ is selected from the group consisting of phenyl, 4-(1-piperidinyl-ethoxy)-phenyl, 4-(1-pyrrolidinyl-ethoxy)-phenyl, 4-(4-morpholinyl-ethoxy)-phenyl, 4-(1-azepinyl-ethoxy)-phenyl, 4-(dimethylamino-ethoxy)-phenyl and 4-(dimethylamino)-phenyl.

In another embodiment of the present invention $R^2$ is selected from the group consisting of -(alkyl)$_{0-4}$-(Q)$_{0-1}$-(alkyl)$_{0-4}$-$NR^D R^E$ and -(alkyl)$_{0-4}$-(Q)$_{0-1}$-(alkyl)$_{0-4}$-C(O)$OR^F$. In yet another embodiment of the present invention, $R^2$ is selected from the group consisting of -(alkyl)$_{0-4}$-(Q)$_{0-1}$-(alkyl)$_{0-4}$-$NR^D R^E$; wherein $R^D$ and $R^E$ are taken together with the nitrogen atom to which they are bound to form a 5 to 7 membered ring selected from the group consisting of heteroaryl and heterocycloalkyl.

In an embodiment of the present invention are compound of formula (I) wherein $R^1$ and $R^2$ are taken together with the carbon atom to which they are bound to form C(O).

In an embodiment of the present invention $R^3$ is selected from the group consisting of halogen, hydroxy, $R^C$, amino, (lower alkyl)-amino, di(lower alkyl)amino, nitro, cyano, —OC(O)$R^G$, —OC(O)O$R^G$, —OC(O)N($R^G$)$_2$, —OSi($R^G$)$_3$—O$R^G$, —O-(alkyl)$_{1-4}$-C(O)$R^G$ and —O-(alkyl)$_{1-4}$-C(O)O$R^G$.

Preferably, $R^3$ is selected from the group consisting of hydroxy, $R^C$, —OC(O)$R^G$, —OC(O)O$R^G$, —OC(O)N($R^G$)$_2$, —OSi($R^G$)$_3$—O$R^G$, —O-(alkyl)$_{1-4}$-C(O)$R^G$ and —O-(alkyl)$_{1-4}$-C(O)O$R^G$.

More preferably, $R^3$ is selected from the group consisting of halogen, hydroxy, lower alkoxy, (lower alkyl-di(lower alkyl))-silyloxy, —OC(O)-(lower alkyl), —OC(O)—C(phenyl)-OC(O)-(lower alkyl), —OC(O)-(1,7,7-trimethyl-2-oxabicyclo[2.2.1]heptan-3-one) and —OC(O)—C(CH$_3$)(CF$_3$)-phenyl. More preferably still $R^3$ is selected from the group consisting of fluoro, hydroxy, methoxy, t-butyl-dimethyl-silyloxy, —OC(O)-t-butyl, —OC(O)—C(phenyl)-OC(O)CH$_3$, —OC(O)-(1,7,7-trimethyl-2-oxabicyclo[2.1]heptan-3-one) and —OC(O)—C(CH$_3$)(CF$_3$)-phenyl. More preferably still, $R^3$ is selected from the group consisting of hydroxy and —OC(O)-t-butyl.

In an embodiment of the present invention $R^G$ is selected from hydrogen, lower alkyl, aryl, aralkyl and 1,7,7-trimethyl-2-oxabicyclo[2.2.1]heptan-3-one; wherein the alkyl, aryl or aralkyl group is optionally substituted with one to two substituents independently selected from lower alkyl, halogenated lower alkyl, lower alkoxy, halogen, hydroxy, nitro, cyano, —OC(O)-(lower alkyl) and —C(O)O-(lower alkyl).

In another embodiment of the present invention two $R^G$ groups are taken together with the nitrogen atom to which they are bound to form a 5 to 6 membered heterocycloalkyl group; wherein the heterocycloalkyl group is optionally substituted with one to two substituents independently selected from halogen, hydroxy, lower alkyl, lower alkoxy, carboxy, amino, (lower alkyl)-amino, di(lower alkyl)amino, nitro or cyano.

In an embodiment of the present invention, m is an integer selected from 0 to 2. Preferably, m is an integer selected from 0 to 1. More preferably m is 1.

In an embodiment of the present invention, m is an integer selected from 1 to 2. Preferably, m is 1.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

As used herein, the term "degenerative brain disease" shall include cognitive disorder, dementia, regardless of underlying cause and Alzheimer's disease.

As used herein, the term "cardiovascular disease" shall include elevated blood lipid levels, coronary arthrosclerosis and coronary heart disease.

As used herein, the term "cerebrovascular disease" shall include abnormal regional cerebral blood flow and ischemic brain damage.

As used herein, the term "progestogen antagonist" shall include mifepristone, J-867 (Jenapharm/TAP Pharmaceuticals), J-956 (Jenapharm/TAP Pharmaceuticals), ORG-31710 (Organon), ORG-32638 (Organon), ORG-31806 (Organon), onapristone and PRA248 (Wyeth).

As used herein, unless otherwise noted, "halogen" shall mean chlorine, bromine, fluorine and iodine.

As used herein, unless otherwise noted, the term "alkyl" whether used alone or as part of a substituent group, include straight and branched chain compositions of one to eight carbon atoms. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1-4 carbon atoms. Similarly, the group "-(alkyl)$_{0-4}$-", whether alone or as part of a large substituent group, shall me the absence of an alkyl group or the presence of an alkyl group comprising one to four carbon atoms. Suitable examples include, but are not limited to —$CH_2$—, —$CH_2CH_2$—, $CH_2$—$CH(CH_3)$—, $CH_2CH_2CH_2$—, —$CH_2CH(CH_3)$ $CH_2$—, $CH_2CH_2CH_2CH_2$—, and the like As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, "aryl" shall refer to unsubstituted carbocyclic aromatic groups such as phenyl, naphthyl, and the like.

As used herein, unless otherwise noted, "aralkyl" shall mean any lower alkyl group substituted with an aryl group such as phenyl, naphthyl and the like. Suitable examples include benzyl, phenylethyl, phenylpropyl, naphthylmethyl, and the like.

As used herein, unless otherwise noted, the term "cycloalkyl" shall mean any stable 3-8 membered monocyclic, saturated ring system, for example cyclopropyl, cyclobutyl, cyclopentyl, cyclohexyl, cycloheptyl and cyclooctyl.

As used herein, unless otherwise noted, the term "cycloalkyl-alkyl" shall mean any lower alkyl group substituted with a cycloalkyl group. Suitable examples include, but are not limited to cyclohexyl-methyl, cyclopentyl-methyl, cyclohexyl-ethyl, and the like.

As used herein, unless otherwise noted, the terms "acyloxy" shall mean a radical group of the formula —O—C(O)—R where R is alkyl, aryl or aralkyl, wherein the alkyl, aryl or aralkyl is optionally substituted. As used herein, the term "carboxylate" shall mean a radical group of the formula —C(O)O—R where R is alkyl, aryl or aralkyl, wherein the alkyl, aryl or aralkyl is optionally substituted.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

As used herein, unless otherwise noted, the term "heteroaryl-alkyl" shall mean any lower alkyl group substituted with a heteroaryl group. Suitable examples include, but are not limited to pyridyl-methyl, isoquinolinyl-methyl, thiazolyl-ethyl, furyl-ethyl, and the like.

As used herein, the term "heterocycloalkyl" shall denote any five to seven membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure.

Examples of suitable heteroaryl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, and the like.

As used herein, unless otherwise noted, the term "heterocycloalkyl-alkyl" shall mean any lower alkyl group substituted with a heterocycloalkyl group. Suitable examples include, but are not limited to piperidinyl-methyl, piperazinyl-methyl, piperazinyl-ethyl, morpholinyl-methyl, and the like.

As used herein, the notation "*" shall denote the presence of a stereogenic center.

When a particular group is "substituted" (e.g., cycloalkyl, aryl, heteroaryl, heterocycloalkyl), that group may have one or more substituents, preferably from one to five substituents, more preferably from one to three substituents, most preferably from one to two substituents, independently selected from the list of substituents. Additionally when aralkyl, heteroaryl-alkyl, heterocycloalkyl-alkyl or cycloalkyl-alkyl group is substituted, the substituent(s) may be on any portion of the group (i.e. the substituent(s) may be on the aryl, heteroaryl, heterocycloalkyl, cycloalkyl or the alkyl portion of the group.)

With reference to substituents, the term "independently" means that when more than one of such substituents is possible, such substituents may be the same or different from each other.

Under standard nomenclature used throughout this disclosure, the terminal portion of the designated side chain is described first, followed by the adjacent functionality toward the point of attachment. Thus, for example, a "phenylC$_1$-C$_6$alkylaminocarbonylC$_1$-C$_6$alkyl" substituent refers to a group of the formula

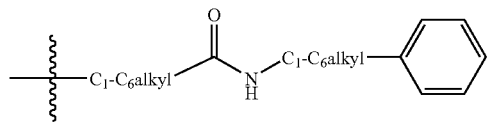

Unless otherwise noted, when naming substituents such as R$^3$ group, the following numbering of the core structure will be applied. The capital letters A, B, C and D will be used to designate specific rings of the tetracyclic core structure.

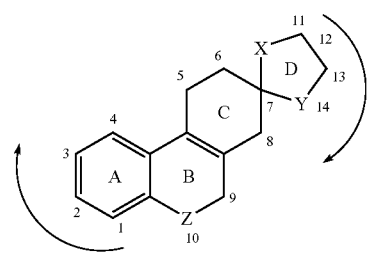

Abbreviations used in the specification, particularly the Schemes and Examples, are as follows
Ac=Acetyl group (—C(O)—CH$_3$)
AD=Alzheimer's disease
CSA=Camphor sulfonic acid
DCC=1,3-Dicyclohexylcarbodiimide
DCM=Dichloromethane
DEAD=Diethylazodicarboxylate
DIAD=Diisopropylazodicarboxylate
Dibal-H=Diisobutyl aluminum hydride
DIC Diisopropylcarbodiimide
DIPEA or DIEA=Diisopropylethylamine
DMA=Dimethylacetamide
DMAP=N,N-Dimethylaminopyridine
DMF=Dimethyl formamide
DMSO=Dimethylsulfoxide
ERT=Estrogen replacement therapy
Et=ethyl (i.e. —CH$_2$CH$_3$)
EtOAc=Ethyl acetate
FBS=Fetal bovine serum
HPLC=High pressure liquid chromatography
HRT=Hormone replacement therapy
IPA=Isopropyl alcohol
iPr$_2$NH=Diisopropylamine
MeOH=Methanol
Ph=Phenyl
PIV or Piv=Pivaloyl
P(Ph)$_3$=Triphenylphosphine
PPTS=Pyridinium p-toluenesulfonate
Rochelle Solution=Aqueous solution of potassium sodium tartrate tetrahydrate
SERM=Selective estrogen receptor modulator
TBAF=Tetra(n-butyl)ammonium fluoride
TBDMS=Tert-butyldimethylsilane
TBS=Tert-butyl-dimethyl-silyl
TBSCl=Tert-butyl-dimethyl-silyl chloride
TEA or Et$_3$N=Triethylamine
TFA=Trifluoroacetic acid
THF=Tetrahydrofuran
TsOH=Tosic acid The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. Wherein the present invention directed to co-therapy comprising administration of one or more compound(s) of formula I and a progestogen or progestogen antagonist, "therapeutically effective amount" shall mean that amount of the combination of agents taken together so that the combined effect elicits the desired biological or medicinal response. For example, the therapeutically effective amount of co-therapy comprising administration of a compound of formula I and progestogen would be the amount of the compound of formula I and the amount of the progestogen that when taken together or sequentially have a combined effect that is therapeutically effective. Further, it will be recognized by one skilled in the art that in the case of co-therapy with a therapeutically effective amount, as in the example above, the amount of the compound of formula I and/or the amount of the progestogen or progestogen antagonist individually may or may not be therapeutically effective.

As used herein, the term "co-therapy" shall mean treatment of a subject in need thereof by administering one or more compounds of formula I with a progestogen or progestogen antagonist, wherein the compound(s) of formula I and progestogen or progestogen antagonist are administered by any suitable means, simultaneously, sequentially, separately or in a single pharmaceutical formulation. Where the compound(s) of formula I and the progestogen or progestogen antagonist are administered in separate dosage forms, the number of dosages administered per day for each compound may be the same or different. The compound(s) of formula I and the progestogen or progestogen antagonist may be administered via the same or different routes of administration. Examples of suitable methods of administration include, but are not limited to, oral, intravenous (iv), intramuscular (im), subcutaneous (sc), transdermal, and rectal. Compounds may also be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices. The compound(s) of formula I and the progestogen or progestogen antagonist may be administered according to simultaneous or alternating regimens, at the same or different times during the course of the therapy, concurrently in divided or single forms.

As used herein, the term "composition" is intended to encompass a product comprising the specified ingredients in the specified amounts, as well as any product which results, directly or indirectly, from combinations of the specified ingredients in the specified amounts.

Compounds of formula (I) wherein X is S, Y is S and Z is O may be prepared

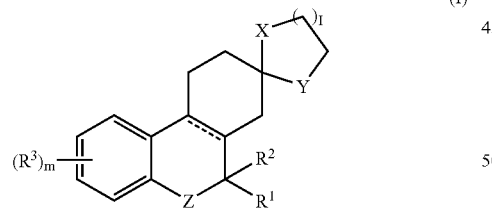

(I)

according to the processes outlined in Scheme 1.

Scheme 1

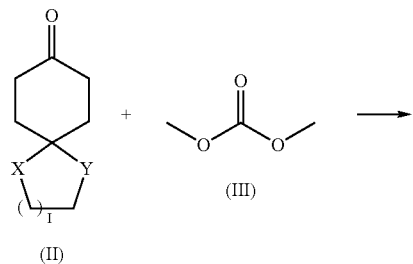

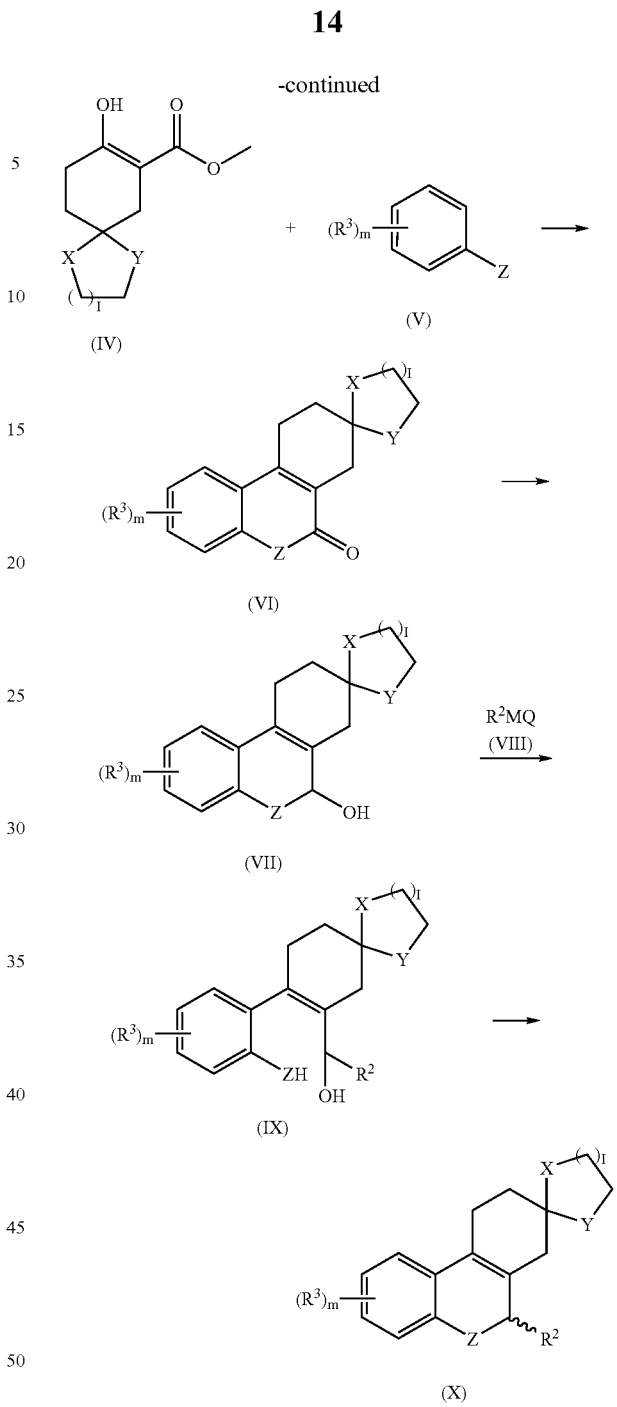

More particularly, a suitably substituted compound of formula (II), where Z is O or S, a known compound or compound prepared by known methods, is reacted with a compound of formula (III), a known compound, in the presence of an organic base such as NaH, NaOMe, t-BuOK, and the like, in an organic solvent such as THF, dioxiane, ethyl ether, and the like, at a temperature in the range of about 0 to about 25° C., to yield the corresponding compound of formula (IV).

The compound of formula (IV) is reacted with a suitably substituted compound of formula (V), a known compound, in the presence of an inorganic acid such as sulfuric acid, hydrochloric acid, and the like or an organic acid such as pTSA, CSA, and like, in an organic solvent such as benzene, toluene, THF, and the like, at a temperature in the range of 0 to about 25° C., to yield the corresponding compound of formula (VI).

One skilled in the art will recognize that it may be necessary and/or desirable to protect one or more of the $R^3$ and/or $R^4$ groups at any of the steps within the process described above. This may be accomplished using known protecting groups and know protection and de-protection reagents and conditions, for example such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991.

Accordingly, the compound of formula (VI) is reacted with diisobutyl-aluminum hydride, L-selectride, and the like, in an organic solvent such as toluene, benzene, THF, methylene chloride, and the like, at a reduced temperature in the range of about 0 to about −80° C., to yield the corresponding compound of formula (VI).

The compound of formula (VII) is reacted with a suitably substituted compound of formula (VIII), wherein MQ is lithium or a magnesium halide such as MgCl, MgBr or MgI, prepared from the corresponding known alkyl or aryl halide by known methods, in an organic solvent such as THF, diethyl ether, dioxane, hexane, and the like, to yield the corresponding compound of formula (IX).

The compound of formula (IX) is treated with a protic acid such as HCl, $H_2SO_4$, p-toluene sulfonic acid, camphor sulfonic acid (CSA), TFA, and the like or a Lewis acid such as $BF_3$ etherate, $AlCl_3$, $SnCl_4$, and the like, in a solvent such as toluene, methylene chloride, acetonitrile and the like, to yield the corresponding compound of formula (X).

Alternatively, the compound of formula (IX) is treated with a reagent such as triphenylphosphine, tributylphosphine, and the like, or an azodicarboxamide such as DEAD, DIAD, and the like, in a solvent such as toluene, THF, and the like, to yield the corresponding compound of formula (X).

Scheme 2

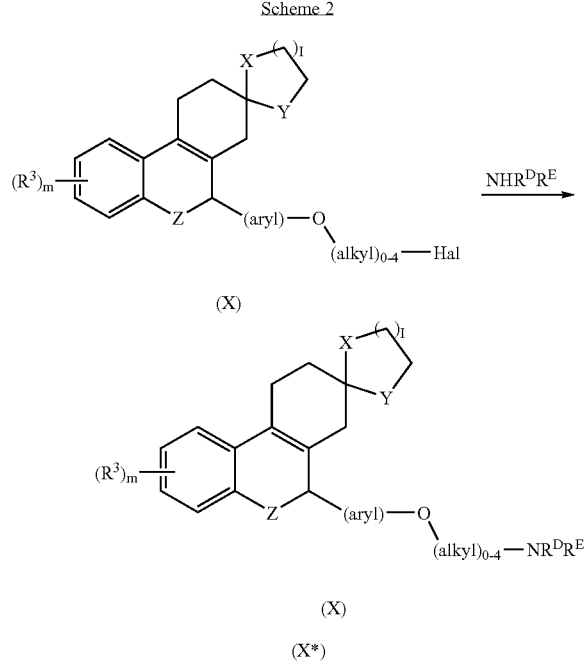

Compounds of formula (X) wherein $R^2$ is -(aryl)-O-(alkyl)$_{0-4}$-NR$^D$R$^E$ may be prepared by reacting a suitably substituted compound of formula (X), wherein the $R^2$ group is -(aryl)-O-(alkyl)$_{0-4}$-Hal (Hal is selected from Cl, Br or I) with a catalytic amount of iodine salt such as NaI, KI, NH$_4$NI, and the like and amine source NHR$^D$R$^E$ such as dimethyl amine, diethyl amine, pyrolidine, piperidine, morphiline and the like, in a solvent such as DMF, DMSO, DMA and the like, to yield the corresponding compound of formula (X). For example, a compound of formula (X*) wherein $R^2$, is -(aryl)-O-(alkyl)$_{0-4}$-NR$^D$R$^E$ may be prepared according to the process outlined in Scheme 2.

One skilled in the art will recognize that it may be necessary and/or desirable to protect one or more of the $R^3$ groups at any of the steps within the process described above. This may be accomplished using known protecting groups and know protection and de-protection reagents and conditions, for example such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991.

Compounds of formula (I) wherein one or more $R^3$ are acyloxy may be prepared by reacting a suitably substituted compound of formula (I), wherein the $R^3$ group(s) are hydroxy with a suitably substituted acid chloride, a suitably substituted carboxylic acid or a suitably substituted anhydride. For example, a compound of formula (I) wherein $R^3$, at the 2 position, is acyloxy may be prepared according to the process outlined in Scheme 3.

Scheme 3

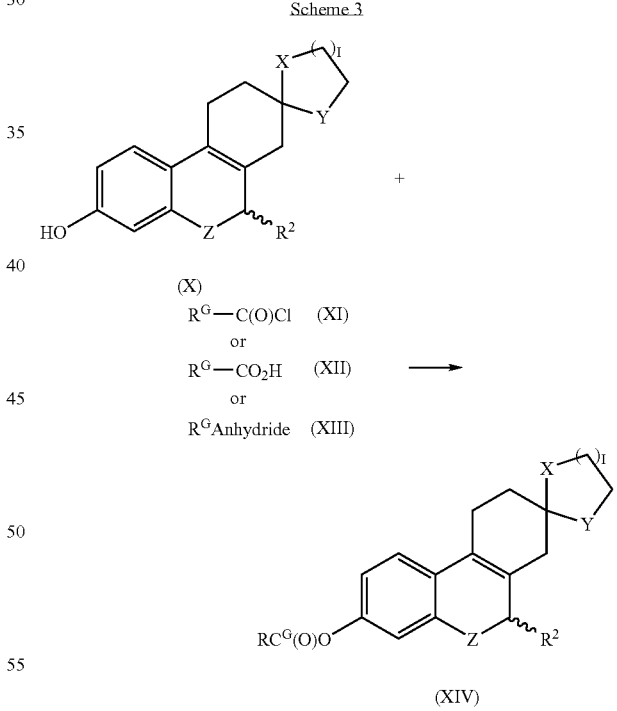

Accordingly, a suitably substituted compound of formula (X) prepared as in Scheme 1, is reacted with a suitably substituted acid chloride, a compound of formula (XI), or a suitably substituted anhydride, a compound of formula (XII), wherein $R^G$ is as defined above, a known compound or compound prepared by known methods, in the presence of an organic amine such as TEA, DIPEA, pyridine, and the like, in a halogenated organic solvent such as DCM, methylene chloride, chloroform, and the like, or in a hydrocarbon solvent such as benzene, toluene, and the like, to yield the corresponding compound of formula (XIV).

Alternatively, the compound of formula (X) is reacted with a suitably substituted carboxylic acid, a compound of formula (VIII), wherein RG is as defined above, a known compound or compound prepared by known methods, in the presence of a coupling reagent such as DCC, DIC, and the like, in an organic solvent such as DMF, THF, methylene chloride, and the like, to yield the corresponding compound of formula (XIV).

Wherein the compound of formula (X), one or more of the $R^3$ groups are hydroxy groups protected with a silyl protecting group such as TBS, the compound of formula (X) is reacted with a tetra-alkyl ammonium fluoride such as TBAF, and the like, and then reacted with a suitably substituted acid chloride of formula (XI), in an organic solvent such as THF, diethyl ether, and the like, to yield the corresponding compound of formula (X).

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

The compound of formula (VI) may be selectively hydrogenated to yield the corresponding compound of formula (XV), as shown in Scheme 4.

Scheme 4

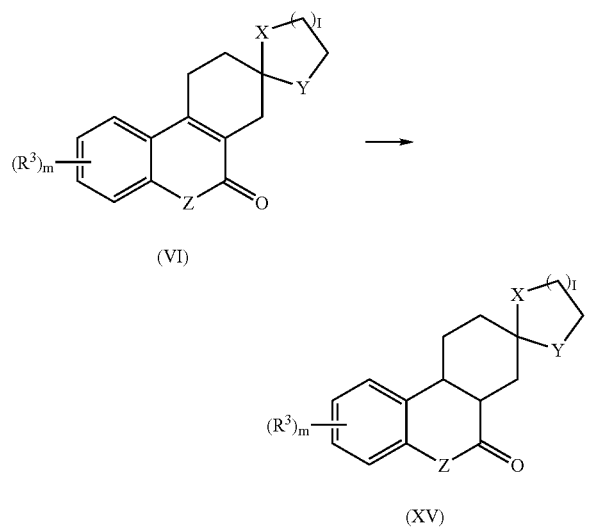

(VI)

(XV)

Accordingly, the compound of formula (VI) is reacted with hydrogen gas, at a pressure in the range of about 20 to about 100 psi, in the presence of a metal catalyst such as Pd on C, Pt on C, Raney nickel, Pd(OH)$_2$, and the like, to yield the corresponding compound of formula (XV), as predominately the cis isomer.

Alternatively, the compound of formula (VI) is reacted with a hydride such as LAH, Cu hydride, SmI$_2$, Stryker's Reagent ([(Ph$_3$P)CuH]$_6$), and the like, in an solvent such as THF, diethyl ether, and the like, at a temperature in the range of about −20 to about 60° C., to yield the corresponding compound of formula (XV), as predominately the trans isomer.

Alternatively still, the compound of formula (VI) is reacted with triethyl silane, in the presence of an acid such as TFA, BF$_3$ etherate, Tin tertachloride, and the like, in an organic solvent such as methylene chloride, toluene, and the like, to yield the corresponding compound of formula (XV), as a mixture of cis and trans isomers.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The utility of the compounds of the instant invention to treat disorders mediated by an estrogen receptor may be determined according to the procedures described in Examples 1-26, and herein.

The present invention therefore provides a method of treating disorders mediated by an estrogen receptor in a subject in need thereof which comprises administering any of the compounds as defined herein in a quantity effective to treat said disorder. The compound may be administered to a patient by any conventional route of administration, including, but not limited to, intravenous, oral, subcutaneous, intramuscular, intradermal and parenteral. The quantity of the compound which is effective for treating a disorder mediated by an estrogen receptor is between 0.01 mg per kg and 20 mg per kg of subject body weight.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 5 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut-oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating a disorder mediated by an estrogen receptor described in the present invention may also be carried out using a pharmaceutical composition comprising any of the compounds as defined herein and a pharmaceutically acceptable carrier. The pharmaceutical composition may contain between about 5 mg and 1000 mg, preferably about 10 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may include suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyl-eneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of a disorder mediated by an estrogen receptor is required.

The daily dosage of the products may be varied over a wide range from 5 to 1,000 mg per adult human per day. For oral administration, the compositions are preferably provided in the form of tablets containing, 1.0, 5.0, 10.0, 15.0, 25.0, 50.0, 100, 250 and 500 milligrams of the active ingredient for the symptomatic adjustment of the dosage to the patient to be treated. An effective amount of the drug is ordinarily supplied at a dosage level of from about 0.01 mg/kg to about 20 mg/kg of body weight per day. Preferably, the range is from about 0.1 mg/kg to about 10 mg/kg of body weight per day, and especially from about 0.5 mg/kg to about 10 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following Examples are set forth to aid in the understanding of the invention, and are not intended and should not be construed to limit in any way the invention set forth in the claims which follow thereafter.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Following the procedures described in the Schemes and Examples above, representative compounds of the present invention were prepared, as listed in Tables 1. For the stereoconfiguration of the $R^2$ group, the R*-(−) and S*-(+) notations indicate that the exact orientation was not determined.

EXAMPLE 1

8-Hydroxy-1,4-dithia-spiro[4.5]dec-7-ene-7-carboxylic Acid Methyl Ester

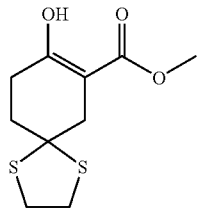

To 1,4-dithia-spiro[4.5]decan-8-one (2.35 g, 12.5 mmoL, 1.0 eq), in THF (10 mL) at 0° C. under nitrogen was added NaH (60%, 2.0 g, 50 mmoL, 4.0 eq) slowly. After gas releasing was completed, dimethy carbonate (11.3 g, 125 mmoL, 10.0 eq) was added via syringe. The reaction mixture was warmed to room temperature and further heated at 50° C. for 2 hours. The reaction was then cooled down to room temperature and quenched with saturated ammonia chloride solution. The solvent was removed in vacuo and the residue was partitioned between ethyl ether and water. The aqueous layer was extracted with ethyl ether twice. The combined organic layer was washed with brine, dried over anhydrous sodium sulfate, filtered and concentrated to give a colorless oil. The crude material was then purified by column chromatography using 5:1 hexanes: ethyl acetate to give the title compound as a colorless solid.

$^1$H NMR ($\delta$, CDCl$_3$) 12.2 (s, 1H), 3.78 (s, 3H), 3.35 (m, 4H), 2.88 (s, 2H), 2.52 (t, J=9.2 Hz, 2H), 2.18 (t, J=9.2 Hz, 2H).

EXAMPLE 2

9-Hydroxy-1,5-dithia-spiro[5.5]undec-8-ene-8-carboxylic Acid Methyl Ester

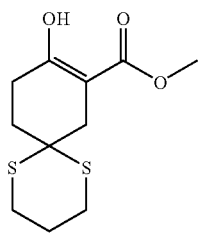

The title product was prepared as a colorless solid according to the procedure described in Example 1 using 1,5-dithiaspiro[5.5]undecan-9-one as the starting material.

$^1$H NMR ($\delta$, CDCl$_3$) 12.2 (s, 1H), 3.80 (s, 3H), 2.95 (m, 4H), 2.66 (s, 2H), 2.45 (t, J=8.5 Hz, 2H), 2.25 (m, 2H), 2.10 (t, J=8.5 Hz, 2H).

EXAMPLE 3

2-Hydroxy-11,14-dithia-spiro[4,5]-5,6,7,8-tetrahydro-benzo[c]chromen-9-one

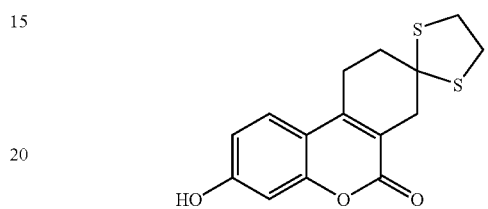

To 8-hydroxy-1,4-dithia-spiro[4.5]dec-7-ene-7-carboxylic acid methyl ester (1.88 g, 7.64 mmoL, 1.0 eq) prepared from Example 1 and resorcinol (841 mg, 7.64 mmoL, 1.0 eq) in CH$_2$Cl$_2$ (10 mL) under nitrogen at, 0° C. was added methyl sulfonic acid (~5 mL). The reaction mixture was stirred at 0° C. for 30 min and then warmed to room temperature. Water and CH$_2$Cl$_2$ were added and the mixture was partitioned between water and CH$_2$Cl$_2$. The aqueous layer was extracted twice with CH$_2$Cl$_2$. The combined organic layer was then washed with saturated sodium bicarbonate solution and brine, dried over anhydrous sodium sulfate, filtered and concentrated to give a brown oil. The crude material was then purified by column chromatography using 4:1 CH$_2$Cl$_2$: MeOH to give the title compound as a yellow semi solid.

$^1$H NMR ($\delta$, CDCl$_3$) 7.55 (d, J=6.8 Hz, 1H), 6.80 (d, J=6.8 Hz, 1H), 6.68 (s, 1H), 3.38 (m, 2H), 3.32 (m, 2H), 3.11 (s, 2H), 3.05 (t, J=10.5 Hz, 2H), 2.28 (t, J=10.5 Hz, 2H). MS 307 MH$^+$, 329 MNa$^+$.

EXAMPLE 4

2-Hydroxy-11,15-dithia-spiro[5,5]-5,6,7,8-tetrahydro-benzo[c]chromen-9-one

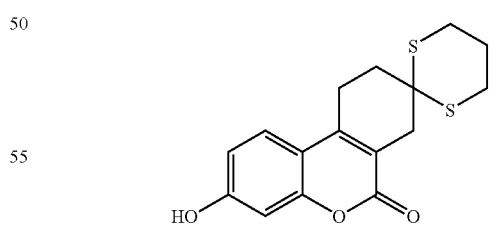

The title product was prepared as a brown solid according to the procedure described in Example 3 using 9-Hydroxy-1, 5-dithia-spiro[5.5]undec-8-ene-8-carboxylic acid methyl ester as the starting material.

$^1$H NMR ($\delta$, CDCl$_3$) 7.58 (d, J=7.5 Hz, 1H), 6.92 (d, J=7.5 Hz, 1H), 6.72 (s, 1H), 3.40 (m, 2H), 3.35 (m, 2H), 3.15 (s, 2H), 3.10 (t, J=9.0 Hz, 2H), 2.50 (t, J=9.0 Hz, 2H), 2.20 (m, 2H). MS 321 MH$^+$, 343 MNa$^+$.

EXAMPLE 5

2-tert-Butyl-dimethyl-silanyloxy-11,14-dithia-spiro[4,5]-5,6,7,8-tetrahydro-benzo[c]chromen-9-one

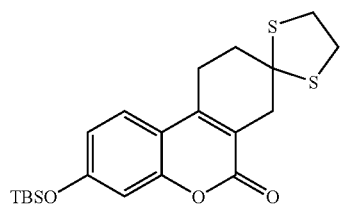

A slurry of 2-hydroxy-10,14-dithia-spiro[4,5]-5,6,7,8-tetrahydro-benzo[c]chromen-9-one (5.72 g, 18.7 mmol, 1 eq), prepared as in Example 3, in DMF (20 mL) was treated with imidazole (1.4 g, 20.6 mmol, 1.1 eq), followed by the addition of t-butyldimethylsilyl chloride (3.1 g, 20.6 mmol, 1.1 eq). The reaction mixture was stirred at room temperature under nitrogen for 18 hours. The reaction mixture was diluted with ethyl ether and washed once with brine. The aqueous washing was re-extracted with ethyl ether twice. The combined organic extracts were dried (anhydrous sodium sulphate), filtered and evaporated in vacuum to yield a yellow solid residue. The solid residue was purified from column chromatography using 5:1 hexane:ethyl acetate to yield the title compound as a light yellow solid.

$^1$H NMR ($\delta$, CDCl$_3$) 7.45 (d, J=7.5 Hz, 1H), 6.78 (m, 2H), 3.45 (m, 4H), 3.21 (s, 2H), 3.05 (t, J=10.5 Hz, 2H), 2.36 (t, J=10.5 Hz, 2H), 1.02 (s, 9H), 0.25 (s, 6H). MS 443 MH$^+$.

EXAMPLE 6

2-Hydroxy-11,15-dithia-spiro[5,5]-5,6,7,8-tetrahydro-benzo[c]chromen-9-one

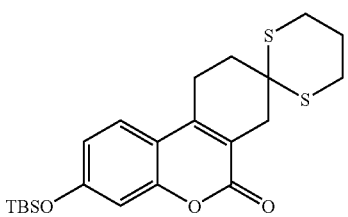

The title product was prepared as a light yellow solid according to the procedure described in Example 5 using 2-Hydroxy-11,15-dithia-spiro[5,5]5,6,7,8-tetrahydro-benzo[c]chromen-9-one as the starting material.

$^1$H NMR ($\delta$, CDCl$_3$) 7.48 (d, J=6.8 Hz, 1H), 6.80 (d, J=6.8 Hz, 1H), 6.78 (s, 1H), 3.40 (m, 2H), 3.20 (s, 2H), 3.03 (t, J=9.0 Hz, 2H), 2.30 (t, J=9.0 Hz, 2H), 2.20 (m, 2H), 1.10 (s, 9H), 0.20 (s, 6H). MS 457 MH$^+$.

EXAMPLE 7

2-(tert-Butyl-dimethyl-silanyloxy)-11,14-dithia-spiro[4,5]-5,6,7,8-tetrahydro-benzo[c]chromen-9-ol

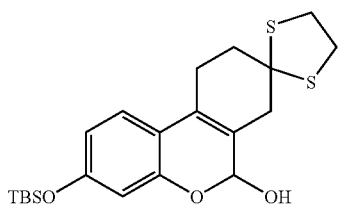

A solution of 2-tert-butyl-dimethyl-silanyloxy-10,14-dithia-spiro[4,5]-5,6,7,8-tetrahydro-benzo[c]chromen-9-one (5.00 g, 11.9 mmol, 1 eq) in toluene (20 mL) was cooled to −78° C. in a 200 mL 3-neck round bottom flask under nitrogen. To the reaction mixture was slowly added a toluene solution of diisobutylaluminum hydride (8.7 mL of 1.5 M, 13.1 mmol, 1.1 eq), with the temperature of the reaction mixture maintained at less than −70° C. The reaction was stirred for 1 hour, quenched with addition of methanol (2 mL). The resulting solution was diluted with dichloromethane, the solution washed with a saturated solution of Rochelle salt, then washed with brine, dried on anhydrous sodium sulphate, filtered and evaporated to yield the crude compound as a yellow solid. The solid was purified by column chromatography using a hexane:ethyl acetate mixture (2:1) to yield the title product as a white solid.

$^1$H NMR ($\delta$, CDCl$_3$) 6.92 (d, J=8.0 Hz, 1H), 6.30 (m, 2H), 5.38 (d, J=6.5 Hz, 1H), 3.21 (m, 4H), 2.85~2.55 (m, 4H), 2.41 (m, 1H), 2.11 (m, 2H), 0.88 (s, 9H), 0.10 (s, 6H), MS 405, [M-H$_2$O]H$^+$.

EXAMPLE 8

2-(tert-Butyl-dimethyl-silanyloxy)-11,15-dithia-spiro[5,5]-5,6,7,8-tetrahydro-benzo[c]chromen-9-ol

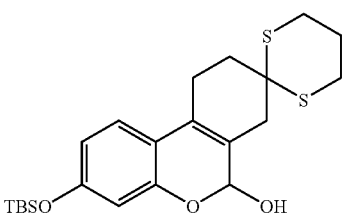

The title product was prepared as a white solid according to the procedure described in Example 7 using 2-Hydroxy-11,15-dithia-spiro[5,5]-5,6,7,8-tetrahydro-benzo[c]chromen-9-one as the starting material.

$^1$H NMR ($\delta$, CDCl$_3$) 6.95 (d, J=6.8 Hz, 1H), 6.32 (s, 1H), 6.28 (m, 1H), 5.36 (d, J=6.5 Hz, 1H), 3.90~2.81 (m, 10H), 1.12 (m, 2H), 0.85 (s, 9H), 0.22 (s, 6H), MS 419, [M-H$_2$O]H$^+$.

EXAMPLE 9

2-(tert-Butyl-dimethyl-silanyloxy)-{9-[4'-(2'-chloro-ethoxy)-phenyl]-11,14-spiro[4,5]-5,6,7,8-tetrahydro-9H-benzo[c]chromene

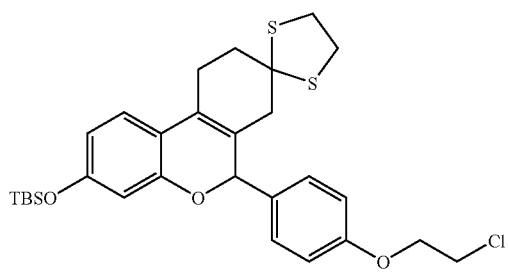

In a single neck, 100 mL round bottom flask was dissolved and stirred 1-(2-chloro-ethoxy)-4-iodo-benzene (3.55 g, 10.7 mmol, 2.0 eq), in tetrahydrofuran (20 mL) under nitrogen, and the mixture cooled to −78° C. After 5 minutes of stirring, a hexane solution of n-BuLi (4.28 mL of 2.5 M, 10.7 mmol, 2.0 eq) was added via syringe. The reaction mixture was then stirred for 30 min at about −78° C. A tetrahydrofuran solution of 2-(tert-butyl-dimethyl-silanyloxy)-10,14-dithia-spiro[4,5]-5,6,7,8-tetrahydro-benzo[c]chromen-9-ol (2.26 g, 5.36 mmol, 1 eq, in 10 mL), prepared as in Example 7, was then added, the cooling bath was removed and the reaction mixture was allowed to warm to room temperature overnight. After about 18 hours, the reaction was worked-up with addition of saturated ammonium acetate solution and extraction with ethyl ether. The combined organic extracts were washed with brine and water, dried with anhydrous sodium sulphate, filtered and evaporated to yield a sticky semisolid residue. To this solid was added 0.5 mL HCl in 20 mL toluene at room temperature. The mixture was stirred for 2 hours at room temperature. The reaction was worked-up with extraction with ethyl acetate three times. The combined organic extracts were washed with brine and water, dried with anhydrous sodium sulphate, filtered and evaporated to yield a brown oil. The title product was isolated as a white semisolid foam via chromatography on silica gel eluted with 2:1 hexanes:ethyl acetate as eluent.

$^1$H NMR (δ, CDCl$_3$) 7.18 (d, J=7.2 Hz, 2H), 6.88 (d, J=7.0 Hz, 1H), 6.72 (d, J=7.2 Hz, 2H), 6.22 (d, J=7.0 Hz, 1H), 6.08 (s, 1H), 5.31 (s, 1H), 4.05 (t, J=11.5 Hz, 2H), 3.62 (t, J=11.5 Hz, 2H), 3.12 (m, 4H), 2.71~2.45 (m, 2H), 2.46~2.20 (abq, J=15.4 Hz, 2H), 2.10 (t, J=10.5 Hz, 2H), 0.72 (s, 9H), 0.12 (s, 6H). MS 561 MH$^+$.

EXAMPLE 10

2-(tert-Butyl-dimethyl-silanyloxy)-{9-[4'-(2'-chloro-ethoxy)-phenyl]-11,15-spiro[5,5]-5,6,7,8-tetrahydro-9H-benzo[c]chromene

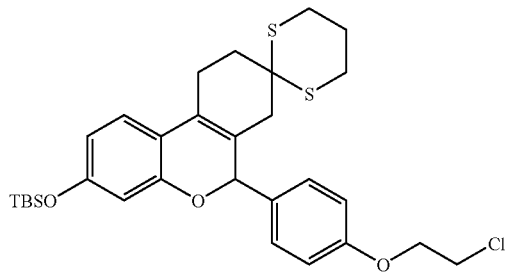

The title product was prepared as a white semisolid according to the procedure described in Example 9 using 2-(tert-Butyl-dimethyl-silanyloxy)-11,15-dithia-spiro[5,5]-5,6,7,8-tetrahydro-benzo[c]chromen-9-ol as the starting material.

$^1$H NMR (δ, CDCl$_3$) 7.15 (d, J=72. Hz, 2H), 6.88 (d, J=6.8 Hz, 1H), 6.72 (d, J=7.2 Hz, 2H), 6.21 (d, J=6.8 Hz, 1H), 6.08 (d, J=1.5 Hz, 1H), 5.32 (s, 1H), 4.05 (t, J=11.2 Hz, 2H), 3.62 (t, J=11.2 Hz, 2H), 2.88-2.48 (m, 3H), 2.45~2.05 (m, 3H), 1.92~1.34 (m, 2H), 1.15 (m, 4H), 0.80 (s, 9H), 0.05 (s, 6H).

EXAMPLE 11

2-(Hydroxy)-{9-[4'-(2'-piperidinyl-ethoxy)-phenyl]-11,14-spiro[4,5]-5,6,7,8-tetrahydro-9H-benzo[c]chromene

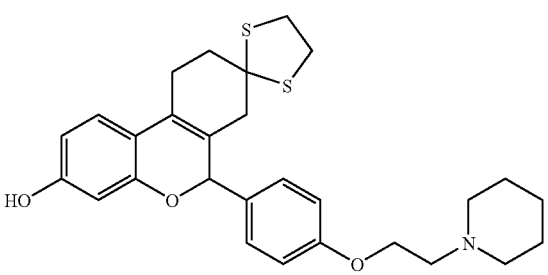

To 2-(tert-butyl-dimethyl-silanyloxy)-{9-[4'-(2'-chloro-ethoxy)-phenyl]-10,14-spiro[4,5]-5,6,7,8-tetrahydro-9H-benzo[c]chromene (250 mg, 0.445 mmoL, 1.0 eq) in DMF (5 mL) was added catalytic amount of KI (8 mg, 0.04 mmoL, 0.1 eq) and piperidine (80 mg, 0.89 mmoL, 2.0 eq). The reaction mixture was heated at 50° C. for 2 hours. CH$_2$Cl$_2$ and water were added, the organic layer was separated and the aqueous layer re-extracted with dichloromethane. The combined organic extracts were washed with brine, dried (anhydrous sodium sulphate), filtered and evaporated in vacuo. The residue was purified by chromatography on silica gel using 2% methanol/dichloromethane as an eluent to yield the title product as a crystalline solid.

$^1$H NMR (δ, CDCl$_3$) 7.25 (d, J=9.0 Hz, 2H), 7.05 (d, J=7.8 Hz, 1H), 6.85 (d, J=9.0 Hz, 2H), 6.32 (d, J=7.8 Hz, 1H), 6.10 (s, 1H), 5.40 (s, 1H), 4.15 (t, J=12.5 Hz, 2H), 3.36 (m, 4H), 3.20 (m, 2H), 2.75 (t, J=12.5 Hz, 2H), 2.58 (m, 4H), 2.55 (m, 2H), 2.25 (t, J=9.8 Hz, 2H), 1.65 (m, 4H), 1.50 (m, 2H).

EXAMPLE 12

2-(Hydroxy)-{9-[4'-(2'-piperidinyl-ethoxy)-phenyl]-11,15-spiro[5,5]-5,6,7,8-tetrahydro-9H-benzo[c]chromene

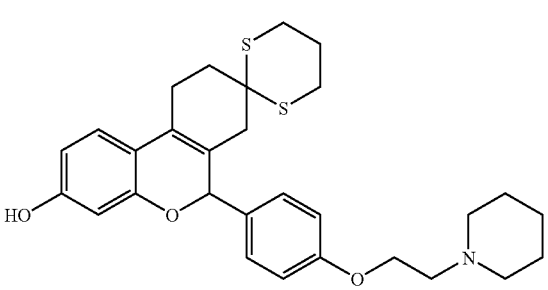

The title product was prepared as a white solid according to the procedure described in Example 11 using 2-(tert-Butyl-dimethyl-silanyloxy)-{9-[4'-(2'-chloro-ethoxy)-phenyl]-11,15-spiro[5,5]-5,6,7,8-tetrahydro-9H-benzo[c]chromene as the starting material.

¹H NMR (δ, CDCl₃) 7.28 (d, J=8.5 Hz, 2H), 6.98 (d, J=8.0 Hz, 1H), 6.70 (d, J=8.5 Hz, 2H), 6.30 (d, J=8.0 Hz, 1H), 6.12 (s, 1H), 5.48 (s, 1H), 4.05 (t, J=17.8 Hz, 2H), 3.05~2.75 (m, 6H), 2.65 (m, 4H), 2.55~2.23 (m, 4H), 2.12~1.88 (m, 4H), 1.72 (m, 4H), 1.48 (m, 2H).

EXAMPLE 13

9R*-2-(Hydroxy)-{9-[4'-(2'-piperidinyl-ethoxy)-phenyl]-11,14-spiro[4,5]-5,6,7,8-tetrahydro-9H-benzo[c]chromene and 9S*-2-(Hydroxy)-{9-[4'-(2'-piperidinyl-ethoxy)-phenyl]-11,14-spiro[4,5]-5,6,7,8-tetrahydro-9H-benzo[c]chromene

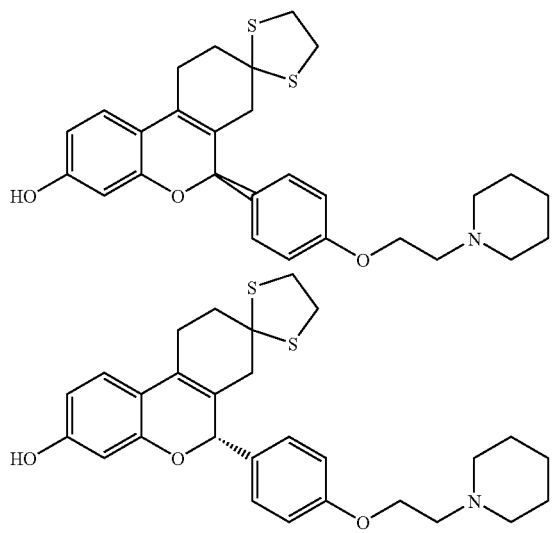

The racemic mixture of (~300 mg) was loaded onto a ChiralPak AD chiral HPLC column (21 mm I.D.×250 mm L) and eluted with 50% methanol in isopropyl alcohol at the 4 mL/min flow rate. Two peaks were collected separately and were removed under vacuum to yield: R* as peak one.

MS(Cl) m/z 496(MH⁺), $[\alpha]_{CDCl3}^{20}$=+16.8.

and S* as peak two.

MS(Cl) m/z 496(MH⁺), $[\alpha]_{CDCl3}^{20}$=−11.5.

EXAMPLE 14

2-(Hydroxy)-{9-[4'-(2'-pyrrolidinyl-ethoxy)-phenyl]-11,14-spiro[4,5]-5,6,7,8-tetrahydro-9H-benzo[c]chromene

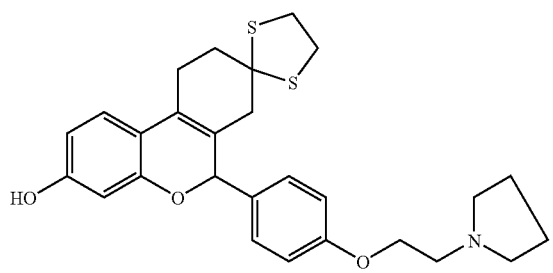

The title product was prepared as a white solid according to the procedure described in Example 11 using pyrolidine as the base.

¹H NMR (δ, CDCl₃) 7.22 (d, J=8.0 Hz, 2H), 7.10 (d, J=6.8 Hz, 1H), 6.85 (d, J=8.0 Hz, 2H), 6.40 (d, J=6.8 Hz, 1H), 6.20 (s, 1H), 5.90 (s, 1H), 4.15 (t, J=10.5 Hz, 2H), 3.40~3.22 (m, 4H), 2.95 (t, J=10.5 Hz, 2H), 2.80~2.65 (m, 4H), 2.58 (m, 4H), 2.55 (m, 2H), 1.85 (m, 4H). MS(Cl) m/z 482 (MH⁺).

EXAMPLE 15

2-(Hydroxy)-{9-[4'-(2'-diethyl-ethoxy)-phenyl]-11,14-spiro[4,5]-5,6,7,8-tetrahydro-9H-benzo[c]chromene

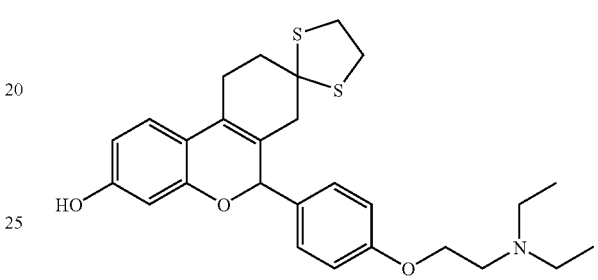

The title product was prepared as a white semisolid according to the procedure described in Example 11 using diethyl amine as the base.

¹H NMR (δ, CDCl₃) 7.25 (d, J=6.5 Hz, 2H), 7.15 (d, J=6.8 Hz, 1H), 6.88 (d, J=6.5 Hz, 2H), 6.48 (d, J=6.8 Hz, 1H), 6.25 (s, 1H), 5.88 (s, 1H), 4.12 (t, J=11.5 Hz, 2H), 3.42~3.20 (m, 4H), 2.85 (t, J=11.5 Hz, 2H), 2.82~2.68 (m, 4H), 2.65 (m, J=12.5 Hz, 4H), 2.55 (m, 2H), 1.15 (t, J=12.5 Hz, 6H), MS(Cl) m/z 484 (MH⁺).

EXAMPLE 16

2",2"-Dimethyl-propionic acid-{9-[4'-(2'-piperidinyl-ethoxy)-phenyl]-11,14-spiro[4,5]-5,6,7,8-tetrahydro-9H-benzo[c]chromen-2-yl Ester

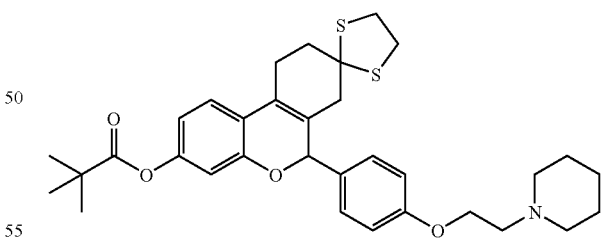

To an ice-cooled and stirred slurry of 2-(hydroxy)-{9-[4'-(2'-piperidinyl-ethoxy)-phenyl]-10,14-spiro[4,5]-5,6,7,8-tetrahydro-9H-benzo[c]chromene (0.2009, 0.404 mmol), prepared as in Example 11, in dichloromethane (5 mL) under nitrogen, was added triethylamine (0.11 mL, 0.808 mmol, 2.0 eq) at 0° C. After about 10 minutes the reaction mixture was observed to become clear. To the reaction mixture was then slowly added (over a period of about 5 minutes) 2,2-dimethylpropionyl chloride (i.e., pivaloyl chloride, 0.075 mL, 0.606 mmol, 1.5 eq.). The cooling bath was then removed and the reaction mixture was allowed to warm to room temperature overnight. To the reaction mixture was then added saturated NaHCO₃ solution and the resulting solution was stirred at room temperature for 1 hour. The organic layer was separated and the aqueous layer re-extracted with dichloromethane. The combined organic extracts were washed with brine, dried (anhydrous sodium sulphate), filtered and evaporated in vacuo. The residue was purified by chromatography on silica gel using 2% methanol/dichloromethane as an eluent to yield the title product as an ivory, crystalline solid.

$^1$H NMR ($\delta$, CDCl₃) 7.26 (d, J=8.5 Hz, 2H), 7.15 (d, J=8.0 Hz, 1H), 6.82 (d, J=8.5 Hz, 2H), 6.60 (d, J=8.0 Hz, 1H), 6.42 (s, 1H), 5.51 (s, 1H), 4.08 (t, J=7.8 Hz, 2H), 3.28 (m, 4H), 2.75 (t, J=7.8 Hz, 2H), 2.70~2.38 (m, 4H), 2.25 (t, J=7.8 Hz, 2H), 1.62 (m, 4H), 1.48 (m, 2H), 1.32 (s, 9H). MS 580 MH⁺, 602 MNa⁺.

EXAMPLE 17

2'',2''-Dimethyl-propionic acid-{9-[4'-(2'-piperidinyl-ethoxy)-phenyl]-11,15-spiro[5,5]-5,6,7,8-tetrahydro-9H-benzo[c]chromen-2-yl Ester

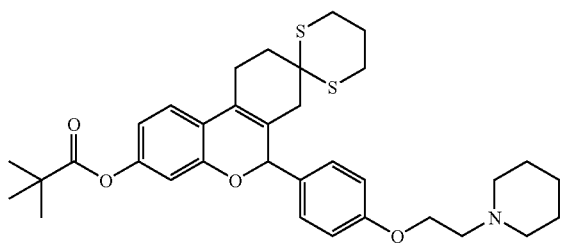

The title product was prepared as a white semisolid according to the procedure described in Example 14 using 2-(Hydroxy)-{9-[4'-(2'-piperidinyl-ethoxy)-phenyl]-11,15-spiro[5,5]-5,6,7,8-tetrahydro-9H-benzo[c]chromene as the starting material.

$^1$H NMR ($\delta$, CDCl₃) 7.28 (d, J=8.4 Hz, 2H), 7.14 (d, J=7.8 Hz, 1H), 6.82 (d, J=8.4 Hz, 2H), 6.60 (d, J=7.8 Hz, 1H), 6.42 (s, 1H), 5.50 (s, 1H), 4.12 (t, J=6.5 Hz, 2H), 3.05~2.76 (m, 4H), 2.80 (t, J=6.5 Hz, 2H), 2.70~2.40 (m, 8H), 2.15~1.88 (m, 4H) 1.68 (m, 4H), 1.48 (m, 2H), 1.30 (s, 9H). MS 594 MH⁺, 616 MNa⁺.

EXAMPLE 18

2-(hydroxy)-{9-[4'-(2'-piperidinyl-ethoxy)-phenyl]-11,15-spiro[5,5]-5,6,7,8-tetrahydro-9H-benzo[c]chrome-11,11,15,15-tetraoxide

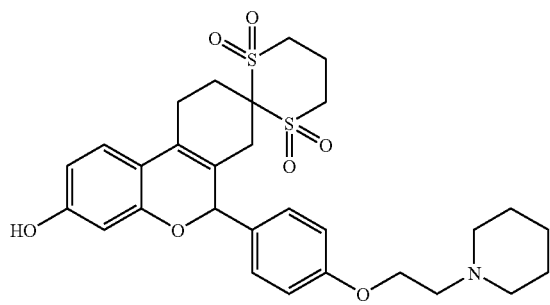

To 2-(hydroxy)-{9-[4'-(2'-piperidinyl-ethoxy)-phenyl]-11,15-spiro[5,5]-5,6,7,8-tetrahydro-9H-benzo[c]chromene (300 mg, 0.521 mmoL, 1.0 eq), prepared from Example 10 in the mixture solution of ethylene glycol (0.5 mL), CH₂Cl₂ (0.5 mL) and acetonitrile (4 mL) at room temperature was added OXONE (640 mg, 1.04 mmoL, 2.0 eq) in one portion. The reaction mixture was stirred for 4 hours at room temperature. The solvent was removed and the residue was partitioned between CH₂Cl₂ and water. The organic layer was separated and the aqueous layer re-extracted with dichloromethane. The combined organic extracts were washed with brine, dried (anhydrous sodium sulphate), filtered and evaporated in vacuo. The residue, KI (8 mg, 0.05 mmoL, 0.1 eq) and piperidine (90 mg, 1.04 mmoL, 2.0 eq) in DMF (5 mL) were heated at 50° C. for 2 hours. The reaction mixture was then partitioned between CH₂Cl₂ and water. The organic layer was washed with brine, dried over anhydrous sodium sulfate then purified by chromatography on silica gel using 2% methanol/dichloromethane as an eluent to yield the title product as an ivory, crystalline solid.

$^1$H NMR ($\delta$, CDCl₃) 7.28 (d, J=8.0 Hz, 2H), 7.10 (d, J=7.5 Hz, 1H), 6.90 (d, J=8.0 Hz, 2H), 6.42 (d, J=7.5 Hz, 1H), 6.12 (s, 1H), 5.45 (s, 1H), 4.10 (t, J=11.5 Hz, 2H), 3.75 (m, 4H), 3.25 (m, 2H), 2.80 (t, J=11.5 Hz, 2H), 2.62 (m, 4H), 2.58 (m, 2H), 2.18 (t, J=8.5 Hz, 2H), 1.55 (m, 4H), 1.48 (m, 2H). MS, 574, MH⁺.

EXAMPLE 19

9R*-2'',2''-Dimethyl-propionic Acid-{9-[4'-(2'-piperidinyl-ethoxy)-phenyl]-11,14-spiro[4,5]-5,6,7,8-tetrahydro-9H-benzo[c]chromen-2-yl Ester and 9S*-2'',2''-Dimethyl-propionic Acid-{9-[4'-(2'-piperidinyl-ethoxy)-phenyl]-11,14-spiro[4,5]-5,6,7,8-tetrahydro-9H-benzo[c]chromen-2-yl Ester

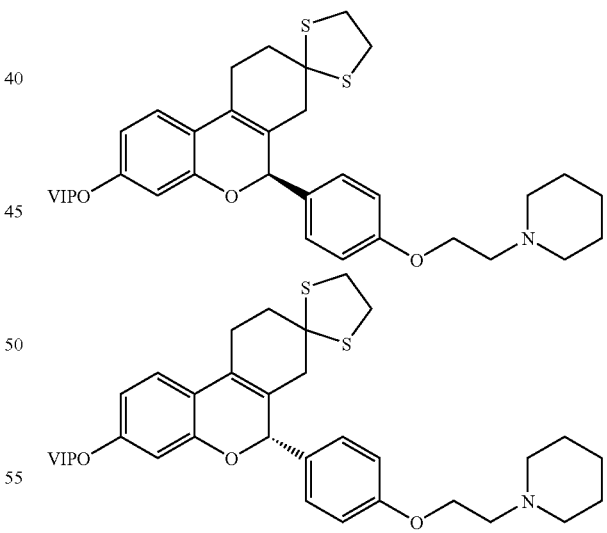

The racemic mixture of (~200 mg) was loaded onto a ChiralPak AD chiral HPLC column (21 mm I.D.×250mm L) and eluted with isopropyl alcohol at the 4 mL/min flow rate. Two peaks were collected separately and were removed under vacuum to yield: R* as peak one.

MS(CI) m/z 580(MH⁺).

and S* as peak two.
MS(CI) m/z 580(MH⁺).

EXAMPLE 20

9R*-2'',2''-Dimethyl-propionic Acid-{9-[4'-(2'-piperidinyl-ethoxy)-phenyl]-11,15-spiro[5,5]-5,6,7,8-tetrahydro-9H-benzo[c]chromen-2-yl Ester and 9S*-2'',2''-Dimethyl-propionic Acid-{9-[4'-(2'-piperidinyl-ethoxy)-phenyl]-11,15-spiro[5,5]-5,6,7,8-tetrahydro-9H-benzo[c]chromen-2-yl Ester

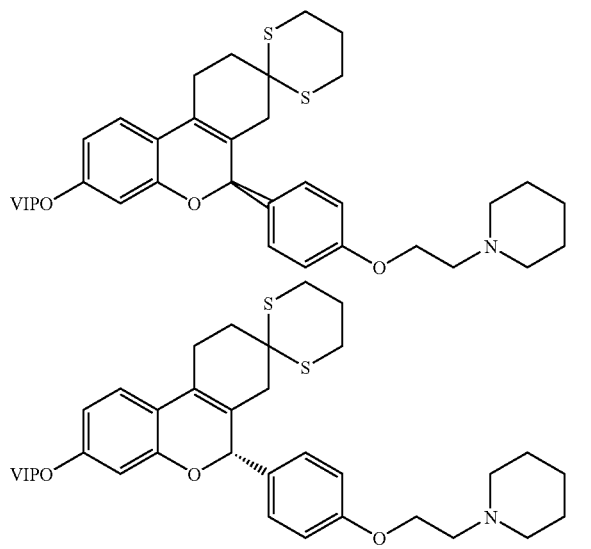

The racemic mixture of (~200 mg) was loaded onto a ChiralPak AD chiral HPLC column (21 mm I.D.×250 mm L) and eluted with isopropyl alcohol at the 4 mL/min flow rate. Two peaks were collected separately and were removed under vacuum to yield: R* as peak one.
MS(CI) m/z 594 (MH+).

and S* as peak two.
MS(CI) m/z 594 (MH+).

EXAMPLE 21

9-[4'-(2'-Piperidin-1'-yl-ethoxy)-phenyl]-9H-benzo[c]chromene-2,7-diol

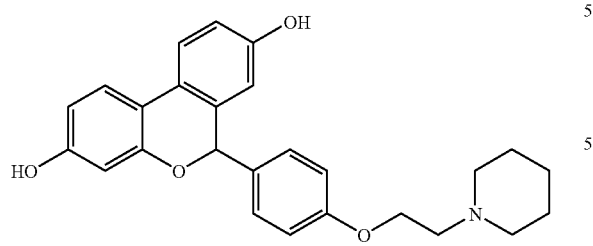

To 2-(Hydroxy)-{9-[4'-(2'-piperidinyl-ethoxy)-phenyl]-10,14-spiro[4,5]-5,6,7,8-tetrahydro-9H-benzo[c]chromene (225 mg, 0.48 mmoL, 1 eq) in THF (5 mL) and water (1 mL) was added Hg(ClO$_4$)$_2$ (4M aqueous solution, 130 mL, 0.52 mmoL, 1.08 eq) followed by CaCO$_3$ (52 mg, 0.52 mmoL, 1.08 eq) at room temperature. The reaction was worked up after 5 min. The solvent was removed and the residue was partitioned between CH$_2$Cl$_2$ and water. The organic layer was separated and the aqueous layer re-extracted with dichloromethane. The combined organic extracts were washed with brine, dried (anhydrous sodium sulphate), filtered and evaporated in vacuo. The residue was purified by chromatography on silica gel using 2% methanol/dichloromethane as an eluent to yield the title product as a white solid.

$^1$H NMR (δ, CDCl$_3$) 7.52 (d, J=6.8 Hz, 2H), 6.88 (d, J=7.0 Hz, 1H), 6.71 (d, J=6.8 Hz, 2H), 6.58 (d, J=7.0 Hz, 1H), 6.52 (s, 1H), 6.62 (s, 1H), 5.88 (s, 1H), 4.05 (t, J=12.5 Hz, 2H), 2.81 (t, J=12.5 Hz, 2H), 2.53 (m, 4H), 1.65 (m, 4H), 1.55 (m, 2H). MS, 443 MNa+.

EXAMPLE 22

2-(tert-Butyl-dimethyl-silanyloxy)-9-[4-(2-chloro-ethoxy)-phenyl]-5,6-dihydro-8H,9H-benzo[c]chromen-7-one

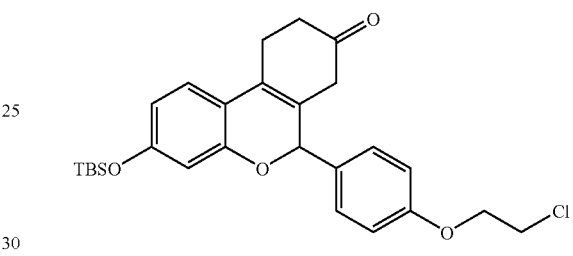

To 2-(tert-butyl-dimethyl-silanyloxy)-{9-[4'-(2'-chloro-ethoxy)-phenyl]-10,14-spiro[4,5]-5,6,7,8-tetrahydro-9H-benzo[c]chromene (310 mg, 0.553 mmoL, 1 eq) in THF (5 mL) and water (1 mL) was added Hg(ClO$_4$)$_2$ (243 mg, 0.608 mmoL, 1.08 eq) followed by CaCO$_3$ (61 mg, 0.608 mmoL, 1.08 eq) at room temperature. The reaction was worked up after 5 min. The solvent was removed and the residue was partitioned between CH$_2$Cl$_2$ and water. The organic layer was separated and the aqueous layer re-extracted with dichloromethane. The combined organic extracts were washed with brine, dried (anhydrous sodium sulphate), filtered and evaporated in vacuo. The residue was purified by chromatography on silica gel using 2% methanol/dichloromethane as an eluent to yield the title product as a white foam.

$^1$H NMR (δ, CDCl$_3$) 7.12 (d, J=12.5 Hz, 2H), 6.91 (d, J=9.5 Hz, 1H), 6.72 (d, J=12.5 Hz, 2H), 6.24 (d, J=9.5 Hz, 1H), 6.12 (s, 1H), 5.36 (s, 1H), 4.05 (t, J=12.5 Hz, 2H), 3.65 (t, J=12.5 Hz, 2H), 2.85~2.45 (m, 6H), 0.82 (s, 9H), 0.02 (s, 6H).

EXAMPLE 23

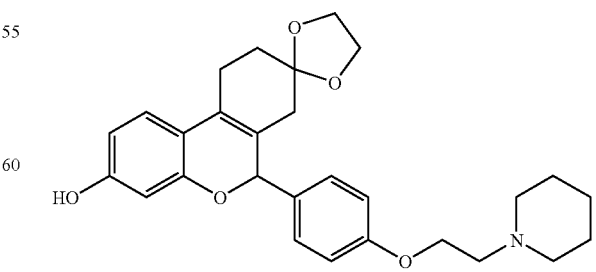

To 2-(tert-Butyl-dimethyl-silanyloxy)-9-[4-(2-chloro-ethoxy)-phenyl]-5,6-dihydro-8H,9H-benzo[c]chromen-7- one (250 mg, 0.52 mmoL, 1.0 eq) in THF (5 mL) at −78° C. was added dropwise of TMSOTf (12. mg, 0.05 mmoL, 0.1 eq) followed by 1,2-bis(trimethylsiloxy)ethane (118 mg, 0.57 mmoL, 1.1 eq). The reaction mixture was stirred at −78° C. for 6 hours and then queched by MeOH (1 mL). The solvent was removed and the residue was partitioned between $CH_2Cl_2$ and water. The organic layer was separated and the aqueous layer re-extracted with dichloromethane. The combined organic extracts were washed with brine, dried (anhydrous sodium sulphate), filtered and evaporated in vacuo. The residue (~200 mg, 0.38 mmoL, 1.0 eq ), KI (7 mg, 0.04 mmoL, 0.1 eq) and piperidine (65 mg, 0.76 mmoL, 2.0 eq) in DMF (5 mL) were heated at 50° C. for 2 hours. The reaction mixture was then partitioned between $CH_2Cl_2$ and water. The organic layer was washed with brine, dried over anhydrous sodium sulfate then purified by chromatography on silica gel using 2% methanol/dichloromethane as an eluent to yield the title product as an ivory, crystalline solid.

$^1$H NMR (δ, $CDCl_3$) 7.30 (d, J=7.8 Hz, 2H), 7.10 (d, J=7.5 Hz, 1H), 6.95 (d, J=7.8 Hz, 2H), 6.42 (d, J=7.5 Hz, 1H), 625 (s, 1H), 5.55 (s, 1H), 4.23 (t, J=12.5 Hz, 2H), 4.05 (m, 4H), 3.25 (m, 2H), 2.84 (t, J=12.5 Hz, 2H), 2.64 (m, 4H), 2.60 (m, 2H), 2.35 (t, J=9.8 Hz, 2H), 1.75 (m, 4H), 1.55 (m, 2H). MS, 464, $MH^+$.

TABLE 1

| ID No | X | Y | R¹/R² | I | R³ | Calc. MW |
|---|---|---|---|---|---|---|
| 3 | S | S | =O | 1 | 2-OH | 306.40 |
| 4 | S | S | =O | 2 | 2-OH | 320.43 |
| 5 | S | S | =O | 1 | 2-OTBS | 420.66 |
| 6 | S | S | =O | 2 | 2-OTBS | 434.69 |
| 7 | S | S | —OH | 1 | 2-OTBS | 422.68 |
| 8 | S | S | —OH | 2 | 2-OTBS | 436.71 |
| 9 | S | S | H/ -C₆H₄-O-CH₂CH₂-Cl | 1 | 2-OTBS | 561.27 |
| 10 | S | S | H/ -C₆H₄-O-CH₂CH₂-Cl | 2 | 2-OTBS | 575.30 |
| 11 | S | S | H/ -C₆H₄-O-CH₂CH₂-piperidine | 1 | 2-OH | 495.70 |
| 12 | S | S | H/ -C₆H₄-O-CH₂CH₂-piperidine | 2 | 2-OH | 509.73 |
| 13 | S | S | H/ -C₆H₄-O-CH₂CH₂-pyrrolidine | 1 | 2-OH | 481.67 |

TABLE 1-continued
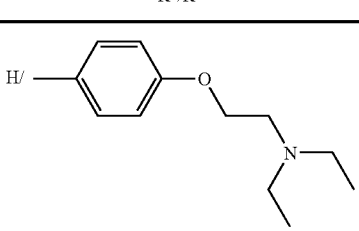
| ID No | X | Y | R¹/R² | I | R³ | Calc. MW |
|---|---|---|---|---|---|---|
| 14 | S | S | 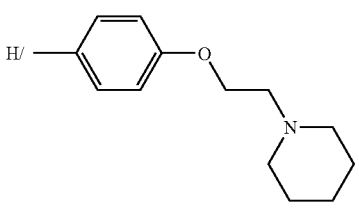 | 1 | 2-OH | 483.69 |
| 15 | S | S | 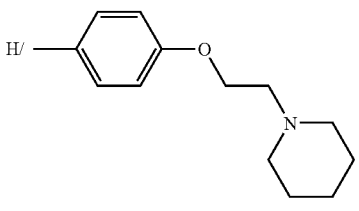 | 1 | 2-OPIV | 579.81 |
| 16 | S | S | 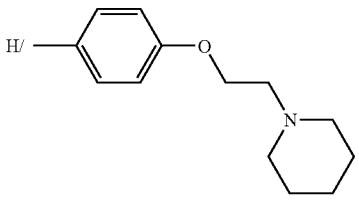 | 2 | 2-OPIV | 593.84 |
| 17 | $SO_2$ | $SO_2$ | 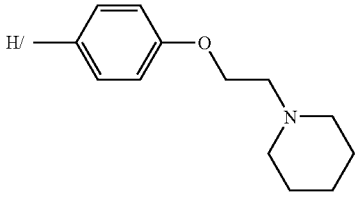 | 2 | 2-OH | 573.73 |
| 18 | O | O | 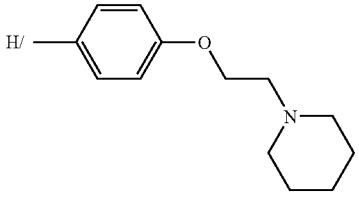 | 1 | 2-OH | 463.57 |
| R*-(+)-11 | S | S | | 1 | 2-OH | 495.70 |

TABLE 1-continued

| ID No | X | Y | R¹/R² | l | R³ | Calc. MW |
|---|---|---|---|---|---|---|
| S*-(−)-11 | S | S | H/ —⟨phenyl⟩—O—CH₂CH₂—N(piperidine) | 1 | 2-OH | 495.70 |
| R*-15 | S | S | H/ —⟨phenyl⟩—O—CH₂CH₂—N(piperidine) | 1 | 2-OPIV | 579.81 |
| S*-15 | S | S | H/ —⟨phenyl⟩—O—CH₂CH₂—N(piperidine) | 1 | 2-OPIV | 579.81 |
| R*-16 | S | S | H/ —⟨phenyl⟩—O—CH₂CH₂—N(piperidine) | 2 | 2-OPIV | 593.84 |
| S*-16 | S | S | H/ —⟨phenyl⟩—O—CH₂CH₂—N(piperidine) | 2 | 2-OPIV | 593.84 |

EXAMPLE 24

MCF-7 Cell Proliferation Assay

This assay was run according to the procedure described by Welshons, et al., (*Breast Cancer Res. Treat.*, 1987, 10(2), 169-75), with minor modification.

Briefly, MCF-7 cells (from Dr. C. Jordan, Northwestern University) were maintained in RPMI 1640 phenol red free medium (Gibco) in 10% FBS (Hyclone), supplemented with bovine insulin and non-essential amino acid (Sigma). The cells were initially treated with 4-hydoxyltamoxifen ($10^{-8}$ M) and let stand at 37° C. for 24 hours. Following this incubation with tamoxifen, the cells were treated with compounds at various concentrations.

Compounds to be tested in the agonist mode were added to the culture media at varying concentrations. Compounds to be treated in the antagonist mode were prepared similarly, and 10 nM 17β-estradiol was also added to the culture media. The cells were incubated for 24 hours at 37° C. Following this incubation, 0.1 µCi of $^{14}$C-thymidine (56 mCi/mmol, Amersham) was added to the culture media and the cells were incubated for an additional 24 hours at 37° C. The cells were then washed twice with Hank's buffered salt solution (HBSS) (Gibco) and counted with a scintillation counter. The increase in the $^{14}$C-thymidine in the compound treated cells relative to the vehicle control cells were reported as percent increase in cell proliferation.

Representative compound of the present invention were tested according to the procedure described above, with results as listed in Table. 2.

TABLE 2

| ID No | Agonist (No.) (nM) | Antagonist (No.) (nM) |
|---|---|---|
| 11 | NA | 1060 |
| 12 | NA | 686 |
| 13 | NA | >10000 |
| 14 | NA | 4970 |
| R*-11 | NA | 672 |
| S*-11 | NA | >10000 |
| R*-15 | NA | 769.5 |
| S*-15 | NA | >10000 |
| R*-16 | NA | 270.7 |
| S*-16 | NA | >10000 |
| 17 | NA | >10000 |

NA indicates no detected activity at test concentration.

EXAMPLE 25

Alkaline Phosphatase Assay in Human Endometrial Ishikawa Cells

This assay was run according to the procedure described by Albert et a., Cancer Res, (9910), 50(11), 330-6-10, with minor modification.

Ishikawa cells (from ATCC) were maintained in DMEM/F12 (1:1) phenol red free medium (Gibco) supplemented with 10% calf serum (Hyclone). 24 hours prior to testing, the medium was changed to DMEM/F12 (1:1) phenol red free containing 2% calf serum.

Compounds to be tested in the agonist mode were added to the culture media at varying concentrations. Compounds to be treated in the antagonist mode were prepared similarly, and 10 nM 17β-estradiol was also added to the culture media. The cells were then incubated at 37° C. for 3 days. On the fourth day, the media was remove, 1 volume of 1× Dilution Buffer (Clontech) was added to the well followed by addition of 1 volume of Assay Buffer (Clontech). The cells were then incubated at room temperature for 5 minutes. 1 volume of freshly prepared Chemiluminescence Buffer (1 volume of chemiluminescent substrate (CSPD) in 19 volume Chemiluminescent Enhancer with final concentration of CSPD at 1.25 mM; Sigma Chemical Co.) was added. The cells were incubated at room temperature for 10 minutes and then quantified on a luminometer. The increase of chemiluminescence over vehicle control was used to calculate the increase in alkaline phosphatase activity.

Representative compound of the present invention were tested according to the procedure described above, with results as listed in Table 3.

TABLE 3

| ID No | Agonist (No.) (nM) | Antagonist (No.) (nM) |
|---|---|---|
| 11 | NA | 29.6 |
| 12 | NA | 35.1 |
| 13 | NA | 1048 |
| 14 | NA | 65.9 |

TABLE 3-continued

| ID No | Agonist (No.) (nM) | Antagonist (No.) (nM) |
|---|---|---|
| R*-11 | NA | 41.9 |
| S*-11 | NA | 1018 |
| R*-15 | NA | 219.5 |
| S*-15 | NA | >10000 |
| R*-16 | NA | 25.8 |
| S*-16 | NA | >10000 |
| 17 | NA | >10000 |

NA indicates no detected activity at test concentration;

EXAMPLE 26

As a specific embodiment of an oral composition, 100 mg of the compound 11, prepared as in Example 11 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A compound of formula (I)

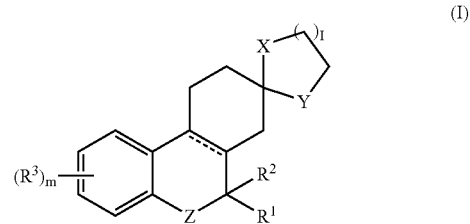

wherein
  ⁓represents a single or double bond,
  X, Y are selected from the group consisting of O, S, SO and $SO_2$;
  Z is selected from the group consisting of O and S;
  $R^1$ is selected from the group consisting of hydrogen, alkyl, cycloalkyl, aryl, aralkyl, heteroaryl and heteroarylalkyl; wherein the cycloalkyl, aryl, aralkyl, heteroaryl or heteroaryl-alkyl group is optionally substituted with one or more substituents independently selected from halogen, hydroxy, alkyl, alkoxy, —SH, —S(alkyl), $SO_2$, $NO_2$, CN, $CO_2H$, $R^C$, —$OR^C$, —$SO_2$—$NR^DR^E$, —N$R^DR^E$, $NR^D$—$SO_2$—$R^F$, -(alkyl)$_{0-4}$-C(O)N$R^DR^E$, (alkyl)$_{0-4}$-$NR^D$—C(O)—$R^F$, -(alkyl)$_{0-4}$-(Q)$_{0-1}$-(alkyl)$_{0-4}$-$NR^DR^E$, -(alkyl)$_{0-4}$-(Q)$_{0-1}$-(alkyl)$_{0-4}$-C(O)—$OR^F$, -(alkyl)$_{0-4}$-(Q)$_{0-1}$-(alkyl)$_{0-4}$-C(O)—$NR^DR^E$ or -(alkyl)$_{0-4}$-C(O)-(alkyl)$_{0-4}$-C(O)—$OR^F$;
  wherein $R^C$ is selected from the group consisting of alkyl, cycloalkyl, cycloalkyl-alkyl, aryl, aralkyl, heteroaryl, heteroaryl-alkyl, heterocycloalkyl and heterocycloalkyl-alkyl; wherein the cycloalkyl, cycloalkyl-alkyl, aryl, aralkyl, heteroaryl, heteroaryl-alkyl, heterocycloalkyl or heterocycloalkyl-alkyl group is optionally substituted with one or more substituents independently selected from halogen, hydroxy, alkyl, alkoxy, —SH, —S(alkyl), $SO_2$, $NO_2$, CN, $CO_2H$, $R^C$, —$SO_2$—$NR^DR^E$, $NR^D$—$SO_2$—$R^F$, -(alkyl)$_{0-4}$-C(O)—$NR^DR^E$, (alkyl)$_{0-4}$—$NR^D$—C(O)—$R^F$, -(alkyl)$_{0-4}$-(Q)$_{0-1}$-(alkyl)$_{0-4}$-$NR^DR^E$, -(alkyl)$_{0-4}$-(Q)$_{0-1}$-(alkyl)$_{0-4}$-

C(O)—OR$^F$, -(alkyl)$_{0-4}$-(Q)$_{0-1}$-(alkyl)$_{0-4}$-C(O)—NR$^D$R$^E$ or -(alkyl)$_{0-4}$-C(O)-(alkyl)$_{0-4}$-C(O)—OR$^F$;

wherein Q is selected from the group consisting of O, S, NH, N(alkyl) and —CH=CH—;

wherein R$^D$ and R$^E$ are each independently selected from the group consisting of hydrogen and alkyl; alternatively R$^D$ and R$^E$ are taken together with the nitrogen atom to which they are bound to form a 4 to 8 membered ring selected from the group consisting of heteroaryl or heterocycloalkyl; wherein the heteroaryl or heterocycloalkyl group is optionally substituted with one or more substituents independently selected from halogen, hydroxy, alkyl, alkoxy, carboxy, amino, alkylamino, dialkylamino, nitro or cyano;

wherein R$^F$ is selected from the group consisting of hydrogen, alkyl, cycloalkyl, cycloalkyl-alkyl, aryl, aralkyl, heteroaryl, heteroaryl-alkyl, heterocycloalkyl and heterocycloalkyl-alkyl; wherein the cycloalkyl, aryl, heteroaryl, heteroaryl-alkyl, heterocycloalkyl or heterocycloalkyl-alkyl group is optionally substituted with one or more substituents independently selected from halogen, hydroxy, alkyl, alkoxy, carboxy, amino, alkylamino, dialkylamino, nitro or cyano;

R$^2$ is selected from the group consisting of hydroxy, alkyl, cycloalkyl, aryl, aralkyl, heteroaryl and heteroaryl-alkyl; wherein the cycloalkyl, aryl, aralkyl, heteroaryl or heteroaryl-alkyl group is optionally substituted with one or more substituents independently selected from halogen, hydroxy, alkyl, alkoxy, —SH, —S(alkyl), SO$_2$, NO$_2$, CN, CO$_2$H, R$^C$, —OR$^C$, —SO$_2$—NR$^D$R$^E$, —NR$^D$R$^E$, NR$^D$—SO$_2$—R$^F$, -(alkyl)$_{0-4}$-C(O)NR$^D$R$^E$, (alkyl)$_{0-4}$-NR$^D$—C(O)—R$^F$, -(alkyl)$_{0-4}$-(Q)$_{0-1}$-(alkyl)$_{0-4}$-NR$^D$R$^E$, -(alkyl)$_{0-4}$-(Q)$_{0-1}$-(alkyl)$_{0-4}$-C(O)—OR$^F$, -(alkyl)$_{0-4}$-(Q)$_{0-1}$-(alkyl)$_{0-4}$-C(O)—NR$^D$R$^E$ or -(alkyl)$_{0-4}$-C(O)-(alkyl)$_{0-4}$-C(O)—OR$^F$;

alternatively, R$^1$ and R$^2$ are taken together with the carbon atom to which they are bound to form C(O);

m is an integer selected from 0 to 4;

R$^3$ is independently selected from the group consisting of halogen, hydroxy, R$^C$, amino, alkylamino, dialkylamino, nitro, cyano, SO$_2$, —C(O)R$^G$, —C(O)OR$^G$, —OC(O)R$^G$, —OC(O)OR$^G$, —OC(O)N(R$^G$)$_2$, —N(R$^G$)C(O)R$^G$, —OSi(R$^G$)$_3$—OR$^G$, —SO$_2$N(R$^G$)$_2$, —O-(alkyl)$_{1-4}$-C(O)R$^G$ and —O-(alkyl)$_{1-4}$-C(O)OR$^G$;

wherein each R$^G$ is independently selected from hydrogen, alkyl, aryl, aralkyl and 1,7,7-trimethyl-2-oxabicyclo[2.2.1]heptan-3-one; wherein the alkyl, aryl or aralkyl group is optionally substituted with one or more substituents independently selected from alkyl, halogenated alkyl, alkoxy, halogen, hydroxy, nitro, cyano, —OC(O)-alkyl or —C(O)O-alkyl;

alternatively two R$^G$ groups are taken together with the nitrogen atom to which they are bound to form a heterocycloalkyl group; wherein the heterocycloalkyl group is optionally substituted with one or more substituents independently selected from halogen, hydroxy, alkyl, alkoxy, carboxy, amino, alkylamino, dialkylamino, nitro or cyano;

I is an integer selected from 0, 1.

2. A compound as in claim 1 wherein

- - - - represents a double bond,

X is S;

Y is S;

Z is O;

R$^1$ is selected from the group consisting of hydrogen and lower alkyl;

R$^2$ is selected from the group consisting of hydroxy, aryl, 4-(1-heterocycloalkyl-alkoxy)-phenyl, 4-(di(alkyl)amino-alkoxy)-phenyl, 4-(di(alkyl)amino)-phenyl and 4-aralkyloxy-phenyl;

alternatively R$^1$ and R$^2$ are taken together with the carbon atom to which they are bound to form C(O);

I is 1;

m is 1;

R$^3$ is selected from the group consisting of halogen, hydroxy, lower alkoxy, (lower alkyl-di(lower alkyl))-silyloxy, —OC(O)-(lower alkyl), —OC(O)—C(phenyl)-OC(O)-(lower alkyl), —OC(O)-(1,7,7-trimethyl-2-oxabicyclo[2.2.1]heptan-3-one) and —OC(O)—C(CH$_3$)(CF$_3$)-phenyl;

and pharmaceutically acceptable salts thereof.

3. A compound as in claim 1 wherein

X is S;

Y is S;

Z is O;

R$^1$ is selected from the group consisting of hydrogen and methyl; R$^2$ is selected from the group consisting of hydroxy, phenyl, 3-(1-piperidinyl-ethoxy)-phenyl, 4-(1-piperidinyl-ethoxy)-phenyl, 4-(1-pyrrolidinyl-ethoxy)-phenyl, 4-(4-morpholinyl-ethoxy)-phenyl, 4-(1-azepinyl-ethoxy)-phenyl, 4-(diethylamino-ethoxy)-phenyl, 4-(dimethylamino-ethoxy)-phenyl, 4-(dimethylamino)-phenyl, 4-benzyloxy-phenyl and 4-(1-piperidinyl-n-propoxy)-phenyl;

alternatively R$^1$ and R$^2$ are taken together with the carbon atom to which they are bound to form C(O);

I=2;

m=1;

R$^3$ is selected from the group consisting of fluoro, hydroxy, methoxy, t-butyl-dimethyl-silyloxy, —OC(O)-t-butyl, —OC(O)—CH(phenyl)-OC(O)CH$_3$, —OC(O)-(1,7,7-trimethyl-2-oxabicyclo[.2.1]heptan-3-one), and —OC(O)—C(CH$_3$)(CF$_3$)-phenyl;

R$^4$ is selected from the group consisting of fluoro, hydroxy, methoxy, t-butyl-dimethyl-silyloxy, —OC(O)-t-butyl, —OC(O)—CH(phenyl)-OC(O)CH$_3$, —OC(O)-(1,7,7-trimethyl-2-oxabicyclo[.2.1]heptan-3-one) and —OC(O)—C(CH$_3$)(CF$_3$)-phenyl;

and pharmaceutically acceptable salts thereof.

4. A compound as in claim 1 wherein

X=O;

Y=O;

Z=O;

R$^1$ is selected from the group consisting of hydrogen and methyl;

R$^2$ is selected from the group consisting of phenyl, 4-(1-piperidinyl-ethoxy)-phenyl, 4-(1-pyrrolidinyl-ethoxy)-phenyl, 4-(4-morpholinyl-ethoxy)-phenyl, 4-(1-azepinyl-ethoxy)-phenyl, 4-(diethylamino-ethoxy)-phenyl, 4-(dimethylamino-ethoxy)-phenyl and 4-(dimethylamino)-phenyl;

alternatively R$^1$ and R$^2$ are taken together with the carbon atom to which they are bound to form C(O);

I=1;

m=1;

R$^3$ is selected from the group consisting of hydroxy and —OC(O)-t-butyl; and pharmaceutically acceptable salts thereof.

5. A compound as in claim 1 wherein

X=O;

Y=O;

Z=O;

R$^1$ is selected from the group consisting of hydrogen and methyl; R$^2$ is selected from the group consisting of phenyl, 4-(1-piperidinyl-ethoxy)-phenyl, 4-(1-pyrrolidinyl-ethoxy)-phenyl, 4-(4-morpholinyl-ethoxy)-phenyl, 4-(1-azepinyl-ethoxy)-phenyl, 4-(diethylamino-ethoxy)-phenyl, 4-(dimethylamino-ethoxy)-phenyl and 4-(dimethylamino)-phenyl;

alternatively $R^1$ and $R^2$ are taken together with the carbon atom to which they are bound to form C(O);
l=2;
m=1;
$R^3$ is selected from the group consisting of hydroxy and —OC(O)-t-butyl; and pharmaceutically acceptable salts thereof.

6. A pharmaceutical composition comprising a pharmaceutically acceptable carrier and a compound of claim 1.

7. A process for making a pharmaceutical composition comprising mixing a compound of claim 1 and a pharmaceutically acceptable carrier.

* * * * *